(12) United States Patent
Ryvkin et al.

(10) Patent No.: US 11,371,094 B2
(45) Date of Patent: Jun. 28, 2022

(54) SYSTEMS AND METHODS FOR NUCLEIC ACID PROCESSING USING DEGENERATE NUCLEOTIDES

(71) Applicant: 10X Genomics, Inc., Pleasanton, CA (US)

(72) Inventors: Paul Ryvkin, San Jose, CA (US); Jason Underwood, Seattle, CA (US); Michael Schnall-Levin, San Francisco, CA (US); Tarjei Mikkelsen, Dublin, CA (US); Benjamin Hindson, Pleasanton, CA (US)

(73) Assignee: 10X Genomics, Inc., Pleasanton, CA (US)

( * ) Notice: Subject to any disclaimer, the term of this patent is extended or adjusted under 35 U.S.C. 154(b) by 38 days.

(21) Appl. No.: 16/818,437

(22) Filed: Mar. 13, 2020

(65) Prior Publication Data

US 2021/0285044 A1    Sep. 16, 2021

Related U.S. Application Data

(63) Continuation-in-part of application No. 15/355,542, filed on Nov. 18, 2016, now abandoned.

(60) Provisional application No. 62/257,438, filed on Nov. 19, 2015.

(51) Int. Cl.
| | | |
|---|---|---|
| C12P 19/34 | (2006.01) | |
| C12Q 1/6874 | (2018.01) | |
| C12Q 1/6806 | (2018.01) | |
| C12Q 1/6851 | (2018.01) | |

(52) U.S. Cl.
CPC ......... *C12Q 1/6874* (2013.01); *C12Q 1/6806* (2013.01); *C12Q 1/6851* (2013.01); *C12Q 2600/156* (2013.01); *C12Q 2600/158* (2013.01)

(58) Field of Classification Search
CPC .................................................. C12Q 1/6869
See application file for complete search history.

(56) References Cited

U.S. PATENT DOCUMENTS

| | | | |
|---|---|---|---|
| 4,124,638 A | 11/1978 | Hansen | |
| 5,185,099 A | 2/1993 | Delpuech et al. | |
| 5,270,183 A | 12/1993 | Corbett et al. | |
| 5,478,893 A | 12/1995 | Ghosh et al. | |
| 5,708,153 A | 1/1998 | Dower et al. | |
| 5,736,330 A | 4/1998 | Fulton | |
| 5,756,334 A | 5/1998 | Perler et al. | |
| 5,846,719 A | 12/1998 | Brenner et al. | |
| 5,900,481 A | 5/1999 | Lough et al. | |
| 5,942,609 A | 8/1999 | Hunkapiller et al. | |
| 5,994,056 A | 11/1999 | Higuchi | |
| 6,033,880 A | 3/2000 | Haff et al. | |
| 6,057,149 A | 5/2000 | Burns et al. | |
| 6,123,798 A | 9/2000 | Gandhi et al. | |
| 6,171,850 B1 | 1/2001 | Nagle et al. | |
| 6,172,218 B1 | 1/2001 | Brenner | |
| 6,176,962 B1 | 1/2001 | Soane et al. | |
| 6,306,590 B1 | 10/2001 | Mehta et al. | |
| 6,327,410 B1 | 12/2001 | Walt et al. | |
| 6,379,929 B1 | 4/2002 | Burns et al. | |
| 6,406,848 B1 | 6/2002 | Bridgham et al. | |
| 6,409,832 B2 | 6/2002 | Weigl et al. | |
| 6,492,118 B1 | 12/2002 | Abrams et al. | |
| 6,524,456 B1 | 2/2003 | Ramsey et al. | |
| 6,586,176 B1 | 7/2003 | Trnovsky et al. | |
| 6,632,655 B1 | 10/2003 | Mehta et al. | |
| 6,806,058 B2 | 10/2004 | Jesperson et al. | |
| 6,890,741 B2 | 5/2005 | Fan et al. | |
| 6,915,679 B2 | 7/2005 | Chien et al. | |
| 7,041,481 B2 | 5/2006 | Anderson et al. | |
| 7,115,400 B1 | 10/2006 | Adessi et al. | |
| 7,129,091 B2 | 10/2006 | Ismagilov et al. | |
| 7,268,167 B2 | 9/2007 | Higuchi et al. | |
| 7,282,370 B2 | 10/2007 | Bridgham et al. | |
| 7,294,503 B2 | 11/2007 | Quake et al. | |
| 7,323,305 B2 | 1/2008 | Leamon et al. | |
| 7,544,473 B2 | 6/2009 | Brenner | |
| 7,622,076 B2 | 11/2009 | Davies et al. | |
| 7,622,280 B2 | 11/2009 | Holliger et al. | |
| 7,638,276 B2 | 12/2009 | Griffiths et al. | |
| 7,645,596 B2 | 1/2010 | Williams et al. | |
| 7,708,949 B2 | 5/2010 | Stone et al. | |

(Continued)

FOREIGN PATENT DOCUMENTS

| | | | |
|---|---|---|---|
| EP | 1019496 B1 | 9/2004 | |
| EP | 1841879 A2 | 10/2007 | |

(Continued)

OTHER PUBLICATIONS

Abate, A.R. et al. "Beating Poisson encapsulation statistics using close-packed ordering" Lab on a Chip (Sep. 21, 2009) 9(18):2628-2631.

Adamson, et al. A Multiplexed Single-Cell CRISPR Screening Platform Enables Systematic Dissection of the Unfolded Protein Response. Cell. Dec. 15, 2016;167(7):1867-1882.e21. doi:10.1016/j.cell.2016.11.048.

Adamson et al., "Production of arrays of chemically distinct nanolitre plugs via repeated splitting in microfluidic devices", Lab Chip 6(9): 1178-1186 (Sep. 2006).

Agasti, S.S. et al. "Photocleavable DNA barcode-antibody conjugates allow sensitive and multiplexed protein analysis in single cell" J Am Chem Soc (2012) 134(45):18499-18502.

(Continued)

*Primary Examiner* — Kenneth R Horlick
(74) *Attorney, Agent, or Firm* — Wilson Sonsini Goodrich & Rosati

(57) ABSTRACT

Provided herein are compositions, systems and methods for tagging molecular events, reactions, species, etc., but without the need for complex, highly diverse libraries of tagging molecules. Provided are tagging moieties that can have a smaller number, a few, or even a single original "tagging" structure that may be transformed or transformable, in situ, into a collection of larger numbers of unique tagging or "barcode" moieties.

13 Claims, 4 Drawing Sheets

(56) References Cited

U.S. PATENT DOCUMENTS

| | | |
|---|---|---|
| 7,772,287 B2 | 8/2010 | Higuchi et al. |
| 7,776,927 B2 | 8/2010 | Chu et al. |
| 7,842,457 B2 | 11/2010 | Berka et al. |
| 7,910,354 B2 | 3/2011 | Drmanac et al. |
| 7,927,797 B2 | 4/2011 | Nobile et al. |
| 7,960,104 B2 | 6/2011 | Drmanac et al. |
| 7,968,287 B2 | 6/2011 | Griffiths et al. |
| 8,003,312 B2 | 8/2011 | Krutzik et al. |
| 8,053,192 B2 | 11/2011 | Bignell et al. |
| 8,133,719 B2 | 3/2012 | Drmanac et al. |
| 8,168,385 B2 | 5/2012 | Brenner |
| 8,268,564 B2 | 9/2012 | Roth et al. |
| 8,273,573 B2 | 9/2012 | Ismagilov et al. |
| 8,298,767 B2 | 10/2012 | Brenner et al. |
| 8,304,193 B2 | 11/2012 | Ismagilov et al. |
| 8,318,433 B2 | 11/2012 | Brenner |
| 8,329,407 B2 | 12/2012 | Ismagilov et al. |
| 8,592,150 B2 | 11/2013 | Drmanac et al. |
| 8,658,430 B2 | 2/2014 | Miller et al. |
| 8,822,148 B2 | 9/2014 | Ismagliov et al. |
| 8,835,358 B2 | 9/2014 | Fodor et al. |
| 8,871,444 B2 | 10/2014 | Griffiths et al. |
| 8,889,083 B2 | 11/2014 | Ismagilov et al. |
| 8,975,302 B2 | 3/2015 | Light et al. |
| 9,012,390 B2 | 4/2015 | Holtze et al. |
| 9,029,083 B2 | 5/2015 | Griffiths et al. |
| 9,029,085 B2 | 5/2015 | Agresti et al. |
| 9,085,798 B2 | 7/2015 | Chee |
| 9,089,844 B2 | 7/2015 | Hiddessen et al. |
| 9,126,160 B2 | 9/2015 | Ness et al. |
| 9,156,010 B2 | 10/2015 | Colston et al. |
| 9,194,861 B2 | 11/2015 | Hindson et al. |
| 9,216,392 B2 | 12/2015 | Hindson et al. |
| 9,238,206 B2 | 1/2016 | Rotem et al. |
| 9,266,104 B2 | 2/2016 | Link |
| 9,273,349 B2 | 3/2016 | Nguyen et al. |
| 9,290,808 B2 | 3/2016 | Fodor et al. |
| 9,328,382 B2 | 5/2016 | Drmanac et al. |
| 9,347,059 B2 | 5/2016 | Saxonov |
| 9,371,598 B2 | 6/2016 | Chee |
| 9,388,465 B2 | 7/2016 | Hindson et al. |
| 9,417,190 B2 | 8/2016 | Hindson et al. |
| 9,486,757 B2 | 11/2016 | Romanowsky et al. |
| 9,498,761 B2 | 11/2016 | Holtze et al. |
| 9,500,664 B2 | 11/2016 | Ness et al. |
| 9,567,631 B2 | 2/2017 | Hindson et al. |
| 9,593,365 B2 | 3/2017 | Frisen et al. |
| 9,623,384 B2 | 4/2017 | Hindson et al. |
| 9,637,799 B2 | 5/2017 | Fan et al. |
| 9,644,204 B2 | 5/2017 | Hindson et al. |
| 9,650,407 B2 | 5/2017 | Gartner et al. |
| 9,689,024 B2 | 6/2017 | Hindson et al. |
| 9,694,361 B2 | 7/2017 | Bharadwaj et al. |
| 9,701,998 B2 | 7/2017 | Hindson et al. |
| 9,764,322 B2 | 9/2017 | Hiddessen et al. |
| 9,824,068 B2 | 11/2017 | Wong |
| 9,868,979 B2 | 1/2018 | Chee et al. |
| 9,879,313 B2 | 1/2018 | Chee et al. |
| 9,946,577 B1 | 4/2018 | Stafford et al. |
| 9,951,386 B2 | 4/2018 | Hindson et al. |
| 9,957,558 B2 | 5/2018 | Leamon et al. |
| 9,975,122 B2 | 5/2018 | Masquelier et al. |
| 10,011,872 B1 | 7/2018 | Belgrader et al. |
| 10,017,759 B2 | 7/2018 | Kaper et al. |
| 10,030,261 B2 | 7/2018 | Frisen et al. |
| 10,059,989 B2 | 8/2018 | Giresi et al. |
| 10,144,950 B2 | 12/2018 | Nolan |
| 10,151,003 B2 | 12/2018 | Fan et al. |
| 10,221,436 B2 | 3/2019 | Hardenbol et al. |
| 10,221,442 B2 | 3/2019 | Hindson et al. |
| 10,246,702 B1 * | 4/2019 | Richard ............. C12N 15/1065 |
| 10,253,364 B2 | 4/2019 | Hindson et al. |
| 10,273,541 B2 | 4/2019 | Hindson et al. |
| 10,323,279 B2 | 6/2019 | Hindson et al. |
| 10,338,066 B2 | 7/2019 | Fan et al. |
| 10,347,365 B2 | 7/2019 | Wong et al. |
| 10,357,771 B2 | 7/2019 | Bharadwaj et al. |
| 10,395,758 B2 | 8/2019 | Schnall-Levin |
| 10,400,280 B2 | 9/2019 | Hindson et al. |
| 10,428,326 B2 | 10/2019 | Belhocine et al. |
| 10,533,221 B2 | 1/2020 | Hindson et al. |
| 10,544,413 B2 | 1/2020 | Bharadwaj et al. |
| 10,549,279 B2 | 2/2020 | Bharadwaj et al. |
| 10,590,244 B2 | 3/2020 | Delaney et al. |
| 10,633,691 B2 | 4/2020 | Wu |
| 10,745,742 B2 | 8/2020 | Bent et al. |
| 10,752,949 B2 | 8/2020 | Hindson et al. |
| 10,774,374 B2 | 9/2020 | Frisen et al. |
| 10,815,525 B2 | 10/2020 | Lucero et al. |
| 10,829,815 B2 | 11/2020 | Bharadwaj et al. |
| 10,874,997 B2 | 12/2020 | Weitz et al. |
| 10,995,333 B2 | 5/2021 | Pfeiffer |
| 2002/0005354 A1 | 1/2002 | Spence et al. |
| 2002/0051971 A1 | 5/2002 | Stuelpnagel et al. |
| 2002/0058332 A1 | 5/2002 | Quake et al. |
| 2002/0065609 A1 | 5/2002 | Ashby |
| 2002/0092767 A1 | 7/2002 | Bjornson et al. |
| 2002/0119455 A1 | 8/2002 | Chan |
| 2002/0119544 A1 | 8/2002 | Yan et al. |
| 2002/0127736 A1 | 9/2002 | Chou et al. |
| 2003/0027214 A1 | 2/2003 | Kamb |
| 2003/0036206 A1 | 2/2003 | Chien et al. |
| 2003/0075446 A1 | 4/2003 | Culbertson et al. |
| 2003/0082587 A1 | 5/2003 | Seul et al. |
| 2003/0089605 A1 | 5/2003 | Timperman |
| 2003/0124509 A1 | 7/2003 | Kenis et al. |
| 2003/0215862 A1 | 11/2003 | Parce et al. |
| 2004/0068019 A1 | 4/2004 | Higuchi et al. |
| 2005/0019839 A1 | 1/2005 | Jespersen et al. |
| 2005/0037397 A1 | 2/2005 | Mirkin et al. |
| 2005/0130188 A1 | 6/2005 | Walt et al. |
| 2005/0250147 A1 | 11/2005 | Macevicz |
| 2005/0266582 A1 | 12/2005 | Modlin et al. |
| 2005/0287572 A1 | 12/2005 | Mathies et al. |
| 2006/0177832 A1 | 8/2006 | Brenner |
| 2006/0275782 A1 | 12/2006 | Gunderson et al. |
| 2006/0286570 A1 | 12/2006 | Rowlen et al. |
| 2007/0009954 A1 | 1/2007 | Wang et al. |
| 2007/0020640 A1 | 1/2007 | McCloskey et al. |
| 2007/0031829 A1 | 2/2007 | Yasuno et al. |
| 2007/0042400 A1 | 2/2007 | Choi et al. |
| 2007/0042419 A1 | 2/2007 | Barany et al. |
| 2007/0172873 A1 | 7/2007 | Brenner et al. |
| 2007/0190543 A1 | 8/2007 | Livak |
| 2007/0196397 A1 | 8/2007 | Torii et al. |
| 2007/0264320 A1 | 11/2007 | Lee et al. |
| 2008/0056948 A1 | 3/2008 | Dale et al. |
| 2008/0166720 A1 | 7/2008 | Hsieh et al. |
| 2008/0242560 A1 | 10/2008 | Gunderson et al. |
| 2009/0011943 A1 | 1/2009 | Drmanac et al. |
| 2009/0047713 A1 | 2/2009 | Handique |
| 2009/0099041 A1 | 4/2009 | Church et al. |
| 2009/0131543 A1 | 5/2009 | Weitz et al. |
| 2009/0148961 A1 | 6/2009 | Luchini et al. |
| 2009/0155563 A1 | 6/2009 | Petsev et al. |
| 2009/0202984 A1 | 8/2009 | Cantor |
| 2009/0235990 A1 | 9/2009 | Beer |
| 2009/0269248 A1 | 10/2009 | Falb et al. |
| 2009/0286687 A1 | 11/2009 | Dressman et al. |
| 2010/0035254 A1 | 2/2010 | Williams |
| 2010/0069263 A1 | 3/2010 | Shendure et al. |
| 2010/0086914 A1 | 4/2010 | Bentley et al. |
| 2010/0105866 A1 | 4/2010 | Fraden et al. |
| 2010/0184928 A1 | 7/2010 | Kumacheva |
| 2010/0216153 A1 | 8/2010 | Lapidus et al. |
| 2010/0248991 A1 | 9/2010 | Roesler et al. |
| 2010/0304982 A1 | 12/2010 | Hinz et al. |
| 2011/0217736 A1 | 9/2011 | Hindson |
| 2011/0263457 A1 | 10/2011 | Krutzik et al. |
| 2011/0305761 A1 | 12/2011 | Shum et al. |
| 2012/0014977 A1 | 1/2012 | Furihata et al. |
| 2012/0071331 A1 | 3/2012 | Casbon et al. |
| 2012/0165219 A1 | 6/2012 | Van et al. |
| 2012/0172259 A1 | 7/2012 | Rigatti et al. |

(56) References Cited

U.S. PATENT DOCUMENTS

| | | |
|---|---|---|
| 2012/0190032 A1 | 7/2012 | Ness et al. |
| 2012/0196288 A1 | 8/2012 | Beer |
| 2012/0219947 A1 | 8/2012 | Yurkovetsky et al. |
| 2012/0231972 A1 | 9/2012 | Golyshin et al. |
| 2012/0252012 A1 | 10/2012 | Armougom et al. |
| 2012/0253689 A1 | 10/2012 | Rogan et al. |
| 2013/0028812 A1 | 1/2013 | Prieto et al. |
| 2013/0109575 A1 | 5/2013 | Kleinschmidt et al. |
| 2013/0225623 A1 | 8/2013 | Buxbaum et al. |
| 2014/0065234 A1 | 3/2014 | Shum et al. |
| 2014/0206073 A1 | 7/2014 | Park et al. |
| 2014/0221239 A1 | 8/2014 | Carman et al. |
| 2014/0235506 A1 | 8/2014 | Hindson et al. |
| 2014/0242664 A1 | 8/2014 | Zhang et al. |
| 2014/0272996 A1 | 9/2014 | Bemis |
| 2014/0274740 A1 | 9/2014 | Srinivasan et al. |
| 2014/0302503 A1 | 10/2014 | Lowe et al. |
| 2014/0315755 A1 | 10/2014 | Chen et al. |
| 2014/0338753 A1 | 11/2014 | Sperling et al. |
| 2014/0357500 A1* | 12/2014 | Vigneault ............ C12Q 1/6874 506/4 |
| 2014/0357530 A1 | 12/2014 | Zhang et al. |
| 2014/0378345 A1 | 12/2014 | Hindson et al. |
| 2015/0005188 A1 | 1/2015 | Levner et al. |
| 2015/0066385 A1 | 3/2015 | Schnall-Levin et al. |
| 2015/0072899 A1 | 3/2015 | Ward et al. |
| 2015/0220532 A1 | 8/2015 | Wong |
| 2015/0267191 A1 | 9/2015 | Steelman et al. |
| 2015/0275289 A1 | 10/2015 | Otwinowski et al. |
| 2015/0361418 A1 | 12/2015 | Reed |
| 2015/0376605 A1 | 12/2015 | Jarosz et al. |
| 2015/0376608 A1 | 12/2015 | Kaper et al. |
| 2015/0376609 A1 | 12/2015 | Hindson et al. |
| 2015/0376700 A1 | 12/2015 | Schnall-Levin et al. |
| 2015/0379196 A1 | 12/2015 | Schnall-Levin et al. |
| 2016/0008778 A1 | 1/2016 | Weitz et al. |
| 2016/0024558 A1 | 1/2016 | Hardenbol et al. |
| 2016/0024572 A1 | 1/2016 | Shishkin et al. |
| 2016/0053253 A1 | 2/2016 | Salathia et al. |
| 2016/0059204 A1 | 3/2016 | Hindson et al. |
| 2016/0060621 A1 | 3/2016 | Agresti et al. |
| 2016/0122753 A1 | 5/2016 | Mikkelsen et al. |
| 2016/0122817 A1 | 5/2016 | Jarosz et al. |
| 2016/0153005 A1 | 6/2016 | Zhang et al. |
| 2016/0201125 A1 | 7/2016 | Samuels et al. |
| 2016/0203196 A1 | 7/2016 | Schnall-Levin et al. |
| 2016/0232291 A1 | 8/2016 | Kyriazopoulou-Panagiotopoulou et al. |
| 2016/0244809 A1 | 8/2016 | Belgrader et al. |
| 2016/0244828 A1 | 8/2016 | Mason |
| 2016/0281160 A1 | 9/2016 | Jarosz et al. |
| 2016/0289669 A1 | 10/2016 | Fan et al. |
| 2016/0289769 A1 | 10/2016 | Schwartz et al. |
| 2016/0314242 A1 | 10/2016 | Schnall-Levin et al. |
| 2016/0348093 A1 | 12/2016 | Price et al. |
| 2017/0009274 A1 | 1/2017 | Abate et al. |
| 2017/0016041 A1 | 1/2017 | Greenfield et al. |
| 2017/0128937 A1 | 5/2017 | Hung et al. |
| 2017/0144161 A1 | 5/2017 | Hindson et al. |
| 2017/0145476 A1 | 5/2017 | Ryvkin et al. |
| 2017/0159109 A1 | 6/2017 | Zheng et al. |
| 2017/0235876 A1 | 8/2017 | Jaffe et al. |
| 2017/0260584 A1 | 9/2017 | Zheng et al. |
| 2018/0030515 A1 | 2/2018 | Regev et al. |
| 2018/0057868 A1 | 3/2018 | Walder et al. |
| 2018/0071695 A1 | 3/2018 | Weitz et al. |
| 2018/0080021 A1 | 3/2018 | Reuter et al. |
| 2018/0080075 A1 | 3/2018 | Brenner et al. |
| 2018/0105808 A1 | 4/2018 | Mikkelsen et al. |
| 2018/0112212 A1 | 4/2018 | Nicol et al. |
| 2018/0208975 A1 | 7/2018 | Peterson et al. |
| 2018/0216162 A1 | 8/2018 | Belhocine et al. |
| 2018/0251825 A1 | 9/2018 | Stoeckius et al. |
| 2018/0273933 A1 | 9/2018 | Gunderson et al. |
| 2018/0312822 A1 | 11/2018 | Lee et al. |
| 2018/0312873 A1 | 11/2018 | Zheng |
| 2018/0320224 A1 | 11/2018 | Gaublomme et al. |
| 2018/0334670 A1 | 11/2018 | Bharadwaj et al. |
| 2018/0340169 A1 | 11/2018 | Belhocine et al. |
| 2018/0371538 A1 | 12/2018 | Blauwkamp et al. |
| 2018/0371545 A1 | 12/2018 | Wong et al. |
| 2019/0040382 A1 | 2/2019 | Steemers et al. |
| 2019/0060890 A1 | 2/2019 | Bharadwaj et al. |
| 2019/0060904 A1 | 2/2019 | Bharadwaj et al. |
| 2019/0060905 A1 | 2/2019 | Bharadwaj et al. |
| 2019/0064173 A1 | 2/2019 | Bharadwaj et al. |
| 2019/0071656 A1 | 3/2019 | Chang et al. |
| 2019/0085391 A1 | 3/2019 | Hindson et al. |
| 2019/0100632 A1 | 4/2019 | Delaney et al. |
| 2019/0127731 A1 | 5/2019 | McDermott |
| 2019/0134633 A1 | 5/2019 | Bharadwaj et al. |
| 2019/0136316 A1 | 5/2019 | Hindson et al. |
| 2019/0153532 A1 | 5/2019 | Bharadwaj et al. |
| 2019/0176152 A1 | 6/2019 | Bharadwaj et al. |
| 2019/0177800 A1 | 6/2019 | Boutet et al. |
| 2019/0249226 A1 | 8/2019 | Bent et al. |
| 2019/0276818 A1 | 9/2019 | Gehring et al. |
| 2019/0323088 A1 | 10/2019 | Boutet et al. |
| 2019/0345636 A1 | 11/2019 | McDermott et al. |
| 2019/0352717 A1 | 11/2019 | Schnall-Levin |
| 2019/0367997 A1 | 12/2019 | Bent et al. |
| 2019/0376118 A1 | 12/2019 | Belhocine et al. |
| 2020/0002763 A1 | 1/2020 | Belgrader et al. |
| 2020/0005902 A1 | 1/2020 | Mellen et al. |
| 2020/0032335 A1 | 1/2020 | Alvarado Martinez |
| 2020/0033237 A1 | 1/2020 | Hindson et al. |
| 2020/0033366 A1 | 1/2020 | Alvarado Martinez |
| 2020/0056223 A1 | 2/2020 | Bell |
| 2020/0105373 A1 | 4/2020 | Zheng |

FOREIGN PATENT DOCUMENTS

| | | |
|---|---|---|
| EP | 1967592 B1 | 4/2010 |
| EP | 2540389 A1 | 1/2013 |
| EP | 2635679 B1 | 4/2017 |
| GB | 2097692 A | 11/1982 |
| GB | 2097692 B | 5/1985 |
| WO | WO-84/02000 | 5/1984 |
| WO | WO-95/30782 | 11/1995 |
| WO | WO-99/52708 | 10/1999 |
| WO | WO-2000008212 A1 | 2/2000 |
| WO | WO-2001002850 A1 | 1/2001 |
| WO | WO-0114589 A2 | 3/2001 |
| WO | WO-0189787 A2 | 11/2001 |
| WO | WO-0190418 A1 | 11/2001 |
| WO | WO-2004002627 A2 | 1/2004 |
| WO | WO-2004065617 A2 | 8/2004 |
| WO | WO-2004069849 A2 | 8/2004 |
| WO | WO-2004091763 A2 | 10/2004 |
| WO | WO-2005021151 A1 | 3/2005 |
| WO | WO-2005040406 A1 | 5/2005 |
| WO | WO-2005049787 A9 | 6/2005 |
| WO | WO-2005082098 A2 | 9/2005 |
| WO | WO-2006040551 A2 | 4/2006 |
| WO | WO-2006078841 A1 | 7/2006 |
| WO | WO-2006086210 A2 | 8/2006 |
| WO | WO-2006096571 A2 | 9/2006 |
| WO | WO-2007081385 A2 | 7/2007 |
| WO | WO-2007081387 A1 | 7/2007 |
| WO | WO-2007089541 A2 | 8/2007 |
| WO | WO-2007133710 A2 | 11/2007 |
| WO | WO-2007140015 A2 | 12/2007 |
| WO | WO-2007147079 A2 | 12/2007 |
| WO | WO-2008021123 A1 | 2/2008 |
| WO | WO-2008109176 A2 | 9/2008 |
| WO | WO-2008121342 A2 | 10/2008 |
| WO | WO-2008134153 A1 | 11/2008 |
| WO | WO-2008150432 A1 | 12/2008 |
| WO | WO-2009011808 A1 | 1/2009 |
| WO | WO-2009015296 A1 | 1/2009 |
| WO | WO-2009085215 A1 | 7/2009 |
| WO | WO-2009152928 A2 | 12/2009 |
| WO | WO-2010033200 A2 | 3/2010 |
| WO | WO-2010104604 A1 | 9/2010 |

(56) References Cited

FOREIGN PATENT DOCUMENTS

| | | |
|---|---|---|
| WO | WO-2010117620 A2 | 10/2010 |
| WO | WO-2010148039 A2 | 12/2010 |
| WO | WO-2011028539 A1 | 3/2011 |
| WO | WO-2011047870 A1 | 4/2011 |
| WO | WO-2011056546 A1 | 5/2011 |
| WO | WO-2011066476 A1 | 6/2011 |
| WO | WO-2012048341 A1 | 4/2012 |
| WO | WO-2012061832 A1 | 5/2012 |
| WO | WO-2012083225 A2 | 6/2012 |
| WO | WO-2012106546 A2 | 8/2012 |
| WO | WO-2012112804 A1 | 8/2012 |
| WO | WO-2012112970 A2 | 8/2012 |
| WO | WO-2012116331 A1 | 8/2012 |
| WO | WO-2012142531 A2 | 10/2012 |
| WO | WO-2012142611 A2 | 10/2012 |
| WO | WO-2012149042 A2 | 11/2012 |
| WO | WO-2012166425 A2 | 12/2012 |
| WO | WO-2012167142 A2 | 12/2012 |
| WO | WO-2013019751 A1 | 2/2013 |
| WO | WO-2013036929 A1 | 3/2013 |
| WO | WO-2013055955 A1 | 4/2013 |
| WO | WO-2013096643 A1 | 6/2013 |
| WO | WO-2013126741 A1 | 8/2013 |
| WO | WO-2014028378 A2 | 2/2014 |
| WO | WO-2014108810 A2 | 7/2014 |
| WO | WO-2014165559 A2 | 10/2014 |
| WO | WO-2014182835 A1 | 11/2014 |
| WO | WO-2014200767 A1 | 12/2014 |
| WO | WO-2015015199 A2 | 2/2015 |
| WO | WO-2015044428 A1 | 4/2015 |
| WO | WO-2015164212 A1 | 10/2015 |
| WO | WO-2016040476 A1 | 3/2016 |
| WO | WO-2016061517 A2 | 4/2016 |
| WO | WO-2016126871 A2 | 8/2016 |
| WO | WO-2016174229 A1 | 11/2016 |
| WO | WO-2017015075 A1 | 1/2017 |
| WO | WO-2017075265 A1 | 5/2017 |
| WO | WO-2017075294 A1 | 5/2017 |
| WO | WO-2017117358 A1 | 7/2017 |
| WO | WO-2017184707 A1 | 10/2017 |
| WO | WO-2017197343 A2 | 11/2017 |
| WO | WO-2018039338 A1 | 3/2018 |
| WO | WO-2018058073 A2 | 3/2018 |
| WO | WO-2018064640 A1 | 4/2018 |
| WO | WO-2018091676 A1 | 5/2018 |
| WO | WO-2018119301 A1 | 6/2018 |
| WO | WO-2018119447 A2 | 6/2018 |
| WO | WO-2018125982 A1 | 7/2018 |
| WO | WO-2018172726 A1 | 9/2018 |
| WO | WO-2018174827 A1 | 9/2018 |
| WO | WO-2018191701 A1 | 10/2018 |
| WO | WO-2018213643 A1 | 11/2018 |
| WO | WO-2018226546 A1 | 12/2018 |
| WO | WO-2018236615 A1 | 12/2018 |
| WO | WO-2019028166 A1 | 2/2019 |
| WO | WO-2019040637 A1 | 2/2019 |
| WO | WO-2019083852 A1 | 5/2019 |
| WO | WO-2019084043 A1 | 5/2019 |
| WO | WO-2019084165 A1 | 5/2019 |
| WO | WO-2019108851 A1 | 6/2019 |
| WO | WO-2019113235 A1 | 6/2019 |
| WO | WO-2019118355 A1 | 6/2019 |
| WO | WO-2019126789 A1 | 6/2019 |
| WO | WO-2019148042 A1 | 8/2019 |
| WO | WO-2019152108 A1 | 8/2019 |
| WO | WO-2019157529 A1 | 8/2019 |
| WO | WO-2019165318 A1 | 8/2019 |
| WO | WO-2019169028 A1 | 9/2019 |
| WO | WO-2019169347 A1 | 9/2019 |
| WO | WO-2019173638 A1 | 9/2019 |
| WO | WO-2019191321 A1 | 10/2019 |
| WO | WO-2019217758 A1 | 11/2019 |
| WO | WO-2020028882 A1 | 2/2020 |
| WO | WO-2020041148 A1 | 2/2020 |
| WO | WO-2020142779 A1 | 7/2020 |
| WO | WO-2020168013 A1 | 8/2020 |
| WO | WO-2020198532 A1 | 10/2020 |
| WO | WO-2021046475 A1 | 3/2021 |
| WO | WO-2021/222302 A1 | 11/2021 |
| WO | WO-2021222301 A | 11/2021 |

OTHER PUBLICATIONS

Amini, S. et al. "Haplotype-resolved whole-genome sequencing by contiguity-preserving transposition and combinatorial indexing" Nature Genetics (2014) 46:1343-1349 doi:10.1038/ng.3119.

Anna et al.: Formation of dispersions using "flow focusing" in microchannels: Applied Physics Letters, vol. 82, No. 3, pp. 364-366 (2003).

Baret, "Surfactants in droplet-based microfluidics" Lab Chip (12(3):422-433 (2012).

Beer et al. On-Chip, Real-Time, Single-Copy Polymerase Chain Reaction in Picoliter Droplets. Anal Chem 79:8471-8475 (2007).

Bentolila, et al. Single-step multicolor fluorescence in situ hybridization using semiconductor quantum dot-DNA conjugates. Cell Biochem Biophys. 2006;45(1):59-70.

Braeckmans et al., Scanning the Code. Modern Drug Discovery. 2003:28-32.

Brenner, et al. "In vitro cloning of complex mixtures of DNA on microbeads: physical separation of differentially expressed cDNAs." Proc Natl Acad Sci U S A. Feb. 15, 2000;97(4):1665-70.

Buchman GW, et al. Selective RNA amplification: a novel method using dUMP-containing primers and uracil DNA glycosylase. PCR Methods Appl. Aug. 1993; 3(1):28-31.

Burns, et al. An Integrated Nanoliter DNA Analysis Device. Science. Oct. 16, 1998;282(5388):484-7.

Burns, et al. Microfabricated structures for integrated DNA analysis. Proc Natl Acad Sci U S A. May 28, 1996; 93(11): 5556-5561.

Burns, et al. The intensification of rapid reactions in multiphase systems using slug flow in capillaries. Lab Chip. Sep. 2001;1(1):10-15. Epub Aug. 9, 2001.

Bystrykh, et al. Generalized DNA barcode design based on Hamming codes. PLoS One. 2012;7(5):e36852. doi: 10.1371/journal.pone.0036852. Epub May 17, 2012.

Chen, et al. Chemical transfection of cells in picoliter aqueous droplets in fluorocarbon oil. Anal Chem. Nov. 15, 2011;83(22):8816-20. doi: 10.1021/ac2022794. Epub Oct. 17, 2011.

Chien et al. "Multiport flow-control system for lab-on-a-chip microfluidic devices", Fresenius J. Anal Chem, 371:106-111 (Jul. 27, 2001).

Chu, et al. Controllable monodisperse multiple emulsions. Angew Chem Int Ed Engl. 2007;46(47):8970-4.

Clausell-Tormos et al., "Droplet-based microfluidic platforms for the encapsulation and screening of mammalian cells and multicellular organisms", Chem. Biol. 15:427-437 (2008).

Cong, et al. Multiplex genome engineering using CRISPR/Cas systems. Science. 339.6121 (Feb. 15, 2013): 819-23. doi: 10.1126/science.1231143. Epub Jan. 3, 2013.

Co-pending U.S. Appl. No. 16/434,076, filed Jun. 6, 2019.
Co-pending U.S. Appl. No. 16/434,084, filed Jun. 6, 2019.
Co-pending U.S. Appl. No. 16/434,102, filed Jun. 6, 2019.
Co-pending U.S. Appl. No. 16/530,930, filed Aug. 2, 2019.

Damean, et al. Simultaneous measurement of reactions in microdroplets filled by concentration gradients. Lab Chip. Jun. 21, 2009;9(12):1707-13. doi: 10.1039/b821021g. Epub Mar. 19, 2009.

Datlinger et al. Pooled CRISPR screening with single-cell transcriptome readout. Nature Methods Advance Online Publication (Jan. 18, 2017). DOI: http://www.nature.com/doifinder/10.1038/nmeth.4177. 10 pages.

Delehanty, et al. Peptides for specific intracellular delivery and targeting of nanoparticles: implications for developing nanoparticle-mediated drug delivery. Ther Deliv. Sep. 2010;1(3):411-33.

Dey, et al. Integrated Genome and Transcriptome Sequencing from the Same Cell. Nature biotechnology 33.3 (2015): 285-289. PMC. Web. Dec. 18, 2017.

(56) References Cited

OTHER PUBLICATIONS

Dixit, et al. Perturb-Seq: Dissecting Molecular Circuits with Scalable Single-Cell RNA Profiling of Pooled Genetic Screens. Cell. Dec. 15, 2016;167(7):1853-1866.e17. doi:10.1016/j.cell.2016.11.038.
Drmanac et al., Sequencing by hybridization (SBH): advantages, achievements, and opportunities. Adv Biochem Eng Biotechnol. 2002;77 :75-101.
Duffy et al., Rapid Protyping of Microfluidic Systems and Polydimethylsiloxane, Anal Chem 70:4974-4984 (1998).
Eastburn, et al. Ultrahigh-throughput mammalian single-cell reverse-transcriptase polymerase chain reaction in microfluidic droplets. Anal Chem. Aug. 20, 2013;85(16):8016-21. doi: 10.1021/ac402057q. Epub Aug. 8, 2013.
Esser-Kahn, et al. Triggered release from polymer capsules. Macromolecules. 2011; 44:5539-5553.
Gaublomme, et al. Nuclei multiplexing with barcoded antibodies for single-nucleus genomics. Nat Commun. Jul. 2, 2019;10(1):2907. doi: 10.1038/s41467-019-10756-2.
Gehring, et al. Highly Multiplexed Single-Cell RNA-seq for Defining Cell Population and Transcriptional Spaces. bioRxiv (2018): 315333.
Gericke, et al. Functional cellulose beads: preparation, characterization, and applications. Chemical reviews 113.7 (2013): 4812-4836.
Guo, et al. Droplet microfluidics for high-throughput biological assays. Lab Chip. Jun. 21, 2012;12(12):2146-55. doi: 10.1039/c2lc21147e. Epub Feb. 9, 2012.
Gyarmati, et al. Reversible disulphide formation in polymer networks: a versatile functional group from synthesis to applications. European Polymer Journal. 2013; 49:1268-1286.
Hashimshony, et al. CEL-Seq: Single-Cell RNA-Seq by Multiplexed Linear Amplification. Cell Rep. Sep. 27, 2012;2(3):666-73. doi: 10.1016/j.celrep.2012.08.003. Epub Aug. 30, 2012.
Holtze, et al. Biocompatible surfactants for water-in-fluorocarbon emulsions. Lab Chip. Oct. 2008;8(10):1632-9. doi: 10.1039/b806706f. Epub Sep. 2, 2008.
"How many species of bacteria are there" (wisegeek.com; accessed Jan. 21, 2014).
Huebner, "Quantitative detection of protein expression in single cells using droplet microfluidics", Chem. Commun. 1218-1220 (2007).
Hug, et al. Measurement of the number of molecules of a single mRNA species in a complex mRNA preparation. J Theor Biol. Apr. 21, 2003;221(4):615-24.
Islam, et al. Highly multiplexed and strand-specific single-cell RNA 5' end sequencing. Nat Protoc. Apr. 5, 2012;7(5):813-28. doi: 10.1038/nprot.2012.022.
Jaitin, et al. Massively parallel single-cell RNA-seq for marker-free decomposition of tissues into cell types. Science. Feb. 14, 2014;343(6172):776-9. doi: 10.1126/science.1247651.
Jarosz, M. et al. "Using 1ng of DNA to detect haplotype phasing and gene fusions from whole exome sequencing of cancer cell lines" Cancer Res (2015) 75(suppl5):4742.
Kaper, et al. Supporting Information for "Whole-genome haplotyping by dilution, amplification, and sequencing." Proc Natl Acad Sci U S A. Apr. 2, 2013;110(14):5552-7. doi: 10.1073/pnas.1218696110. Epub Mar. 18, 2013.
Kaper, et al. Whole-genome haplotyping by dilution, amplification, and sequencing. Proc Natl Acad Sci U S A. Apr. 2, 2013;110(14):5552-7. doi: 10.1073/pnas.1218696110. Epub Mar. 18, 2013.
Kenis, et al. Microfabrication Inside Capillaries Using Multiphase Laminar Flow Patterning. Science. 1999; 285:83-85.
Kester, et al. Single-Cell Transcriptomics Meets Lineage Tracing. Cell Stem Cell. Aug. 2, 2018;23(2):166-179. doi: 10.1016/j.stem.2018.04.014. Epub May 10, 2018.
Kivioja, et al. Counting absolute numbers of molecules using unique molecular identifiers. Nat Methods. Nov. 20, 20119(1):72-4.
Klein, et al. Droplet barcoding for single-cell transcriptomics applied to embryonic stem cells. Cell. May 21, 2015; 161:1187-1201.
Korlach et al., Methods in Enzymology, Real-Time DNA Sequencing from Single Polymerase Molecules, (2010) 472:431-455.
Koster et al., "Drop-based microfluidic devices for encapsulation of single cells", Lab on a Chip The Royal Soc. of Chem. 8:1110-1115 (2008).
Lagally, et al. Single-Molecular DNA Amplification and Analysis in an Integrated Microfluidic Device. Anal Chem. Feb. 1, 2001;73(3):565-70.
Lee, et al., Highly Multiplexed Subcellular RNA Sequencing in Situ. Science 343.6177 (Mar. 2014): 1360-1363, doi: 10.1126/science.1250212.
Lennon et al. A scalable, fully automated process for construction of sequence-ready barcoded libraries for 454. Genome Biology 11:R15 (2010).
"List of sequenced bacterial genomes" (Wikipedia.com; accessed Jan. 24, 2014).
Love, "A microengraving method for rapid selection of single cells producing antigen-specific antibodies", Nature Biotech, 24:6 703 (Jun. 2006).
Macaulay, et al. G&T-seq: parallel sequencing of single-cell genomes and transcriptomes. Nature Methods, 2015, p. 1-7.
Macaulay, et al. Single-Cell Multiomics: Multiple Measurements from Single Cells. Trends in Genetics 33.2 (2017): 155-168. PMC. Web. Dec. 18, 2017.
Macosko, et al. Highly Parallel Genome-wide Expression Profiling of Individual Cells Using Nanoliter Droplets. Cell. May 21, 2015;161(5):1202-14. doi: 10.1016/j.cell.2015.05.002.
Madl, et al. "Bioorthogonal Strategies for Engineering Extracellular matrices", Madal, Chritopher, Adv. Funct. Master. Jan. 19, 2018, vol. 28, 1706046, pp. 1-21.
Mair, et al. Injection molded microfluidic chips featuring integrated interconnects. Lab Chip. Oct. 2006;6(10): 1346-54. Epub Jul. 31, 2006.
Mazutis, et al. Single-Cell Analysis and Sorting Using Droplet-Based Microfluidics. Nat Protoc. 8(5): 870-891 (May 2013).
McCoy, R. et al. "Illumina TruSeq Synthetic Long-Reads Empower De Novo Assembly and Resolve Complex, Highly-Repetitive Transposable Elements" PLOS (2014) 9(9):e1016689.
McGinnis et al. MULTI-seq: sample multiplexing for single-cell RNA sequencing using lipid-tagged indices. Nat Methods. Jul. 2019;16(7):619-626. doi: 10.1038/s41592-019-0433-8. Epub Jun. 17, 2019.
McGinnis, et al. MULTI-seq: Scalable sample multiplexing for single-cell RNA sequencing using lipid-tagged indices. bioRxiv (2018) 387241; doi: https://doi.org/10.1101/387241.
Microfluidic ChipShop. Microfluidic product catalogue. Oct. 2009.
Mimitou, et al. Expanding the CITE-seq tool-kit: Detection of proteins, transcriptomes, clonotypes and CRISPR perturbations with multiplexing, in a single assay. bioRxiv preprint first posted online Nov. 8, 2018; doi: http://dx.doi.org/10.1101/466466.
Navin. The first five years of single-cell cancer genomics and beyond. Genome Res. Oct. 2015;25(10):1499-507. doi: 10.1101/gr.191098.115.
Nisisako, et al. Droplet formation in a microchannel network. Lab Chip. Feb. 2002;2(1):24-6. Epub Jan. 18, 2002.
Nisisako, T. et al. Droplet Formation in a Microchannel on PMMA Plate. Micro Total Analysis Systems. 2001. Kluwer Academic Publishers. pp. 137-138.
Nisisako, T. et al., Microfluidics large-scale integration on a chip for mass production of monodisperse droplets and particles, The Royal Society of Chemistry: Lab Chip, (Nov. 23, 2007) 8:287-293.
Novak, R. et al., "Single cell multiplex gene detection and sequencing using microfluidicallygenerated agarose emulsions" Angew. Chem. Int. Ed. Engl. (2011) 50(2):390-395.
Orakdogen, N. "Novel responsive poly(N,N-dimethylaminoethyl methacrylate) gel beads: preparation, mechanical properties and pH-dependent swelling behavior" J Polym Res (2012) 19:9914.
Perrott, Jimmy. Optimization and Improvement of Emulsion PCR for the Ion Torrent Next-Generation Sequencing Platform. (2011) Thesis.
Peters, B.A. et al. Accurate whole-genome sequencing and haplotyping from 10 to 20 human cells. Nature, 487(7406):190-195 (Jul. 11, 2012).

(56) References Cited

OTHER PUBLICATIONS

Plunkett, et al. Chymotrypsin responsive hydrogel: application of a disulfide exchange protocol for the preparation of methacrylamide containing peptides. Biomacromolecules. Mar.-Apr. 2005;6(2):632-7.
Priest, et al. Generation of Monodisperse Gel Emulsions in a Microfluidic Device, Applied Physics Letters, 88:024106 (2006).
Pushkarev et al. "Single-molecule sequencing of an individual human genome," Nature Biotech (2009) 17:847-850.
Ramsey, J.M. "The burgeoning power of the shrinking laboratory" Nature Biotech (1999) 17:1061-1062.
Ramskold et al. (2012) "Full-length mRNA-Seq from single-cell levels of RNA and individual circulating tumor cells" Nature Biotechnology 30(8):777-782.
Roche. Using Multiplex Identifier (MID) Adaptors for the GS FLX Titanium Chemistry Basic MID Set Genome Sequencer FLX System, Technical Bulletin 004-2009, (Apr. 1, 2009) pp. 1-7. URL:http://454.com/downloads/my454/documentation/technical-bulletins/TCB-09004 Using MultiplexIdentifierAdaptorsForTheGSFLXTitaniumSeriesChemistry-BasicMIDSet.pdf.
Rosenberg, et al. Single-cell profiling of the developing mouse brain and spinal cord with split-pool barcoding. Science. Apr. 13, 2018;360(6385):176-182. doi: 10.1126/science.aam8999. Epub Mar. 15, 2018.
Rotem, A. et al., "High-throughput single-cell labeling (Hi-SCL) for RNA-Seq using drop-based microfluidics" PLOS One (May 22, 2015) 0116328 (14 pages).
Saikia, et al. Simultaneous multiplexed amplicon sequencing and transcriptome profiling in single cells. Nat Methods. Jan. 2019;16(1):59-62. doi: 10.1038/s41592-018-0259-9. Epub Dec. 17, 2018.
Schmidt, et al. Quantitative analysis of synthetic cell lineage tracing using nuclease barcoding. ACS synthetic biology 6.6 (2017): 936-942.
Schubert, et al. Microemulsifying fluorinated oils with mixtures of fluorinated and hydrogenated surfactants. Colloids and Surfaces A; Physicochemical and Engineering Aspects, 84(1994) 97-106.
Seiffert, et al. Microfluidic fabrication of smart microgels from macromolecular precursors. 2010. Polymer.
Seiffert, S. et al., "Smart microgel capsules from macromolecular precursors" J. Am. Chem. Soc. (2010) 132:6606-6609.
Shah, "Fabrication of mono disperse thermosensitive microgels and gel capsules in micro fluidic devices", Soft Matter, 4:2303-2309 (2008).
Shahi, et al. Abseq: Ultrahigh-throughput single cell protein profiling with droplet microfluidic barcoding. Sci Rep. 2017; 7: 44447. Published online Mar. 14, 2017. doi: 10.1038/srep44447.
Shendure, et al. Accurate Multiplex Polony Sequencing of an Evolved Bacterial Genome. Science 309.5741 (Sep. 2005): 1728-1732. XP002427180, ISSN: 0036-8075, DOI: 10.1126/SCIENCE.1117839.
Smith, et al. Highly-multiplexed barcode sequencing: an efficient method for parallel analysis of pooled samples. Nucleic Acids Research, 38(13): e142 (2010).
Song, et al. Reactions in droplets in microfluidic channels. Angew Chem Int Ed Engl. Nov. 13, 2006;45(44):7336-56.
Srivatsan, et al. Massively multiplex chemical transcriptomics at single-cell resolution. Science (New York, NY) 367.6473 (2020): 45-51.
Stoeckius, et al. Cell Hashing with barcoded antibodies enables multiplexing and doublet detection for single cell genomics. Genome Biol. Dec. 19, 2018;19(1):224. doi: 10.1186/s13059-018-1603-1.
Stoeckius, et al. Large-scale simultaneous measurement of epitopes and transcriptomes in single cells. bioRxiv 113068; doi: https://doi.org/10.1101/113068; (Mar. 2, 2017).
Stoeckius, et al. Simultaneous epitope and transcriptome measurement in single cells. Nature methods. Jul. 31, 2017. Supplemental Materials.
Thaxton, C.S. et al. "A Bio-Bar-Code Assay Based Upon Dithiothreitol Oligonucleotide Release" Anal Chem (2005) 77:8174-8178.
Theberge, et al. Microdroplets in microfluidics: an evolving platform for discoveries in chemistry and biology. Angew Chem Int Ed Engl. Aug. 9, 2010;49(34):5846-68. doi: 10.1002/anie.200906653.
Thorsen, et al. Dynamic pattern formation in a vesicle-generating microfluidic device. Physical Review Letters. American Physical Society. 2001; 86(18):4163-4166.
Tonelli, et al. Perfluoropolyether functional oligomers: unusual reactivity in organic chemistry. Journal of fluorine chemistry. 2002; 118(1)107-121.
Turchinovich, et al. "Capture and Amplification by Tailing and Switching (CATS): An Ultrasensitive Ligation-Independent Method for Generation of DNA Libraries for Deep Sequencing from Picogram Amounts of DNA and RNA." RNA Biology 11.7 (2014): 817-828. PMC. Web. Nov. 13, 2017.
Ullal et al. Cancer Cell Profiling by Barcoding Allows Multiplexed Protein Analysis in Fine-Needle Aspirates. Sci Transl Med. Jan. 15, 2014; 6(219): 219ra9.
Uttamapinant, et al. Fast, cell-compatible click chemistry with copper-chelating azides for biomolecular labeling.Angew. Chem. Int. End. Engl., Jun. 11, 2012: 51(24) pp. 5852-5856.
Wagner, et al. Biocompatible fluorinated polyglycerols for droplet microfluidics as an alternative to PEG-based copolymer surfactants. Lab Chip. Jan. 7, 2016;16(1):65-9. doi: 10.1039/c5lc00823a. Epub Dec. 2, 2015.
Weigl, et al. Microfluidic Diffusion-Based Separation and Detection. Science. 1999; pp. 346-347.
Williams, et al. Amplification of complex gene libraries by emulsion PCR. Nature Methods. 2006;3(7):545-50.
Wong, et al. Multiplexed Barcoded CRISPR-Cas9 Screening Enabled By CombiGEM. PNAS. Mar. 1, 2016, vol. 113, pp. 2544-2549.
Zhang, et al. One-step fabrication of supramolecular microcapsules from microfluidic droplets. Science. Feb. 10, 2012;335(6069):690-4. doi: 10.1126/science.1215416.
Zhang, et al. Reconstruction of DNA sequencing by hybridization. Bioinformatics. Jan. 2003;19(1):14-21.
Zheng, et al. Massively parallel digital transcriptional profiling of single cells. Nat Commun. Jan. 16, 2017;8:14049. doi: 10.1038/ncomms14049.
Zheng, X.Y. et al. "Haplotyping germline and cancer genomes with high-throughput linked-read sequencing" Nature Biotech (Feb. 1, 2016) 34(3):303-311.
Zhu, et al. Reverse transcriptase template switching: a SMART approach for full-length cDNA library construction. Biotechniques. Apr. 2001;30(4):892-7.
10X Genomics, Inc. CG000153 Rev A. Chromium Single Cell DNA Reagent Kits User Guide. 2018.
10X Genomics, Inc. CG000184 Rev A. Chromium Single Cell 3' Reagent Kits v3 User Guide with Feature Barcoding Technology for CRISPR Screening. 2018.
10X Genomics, Inc. CG000185 Rev B. Chromium Single Cell 3' Reagent Kits User Guide with Feature Barcoding Technology for Cell Surface Protein. 2018.
10X Genomics, Inc. CG000208 Rev E. Chromium Next GEM Single Cell V(D)J reagent Kits v1.1 User Guide with Feature Barcode Technology for Cell Surface Protein. 2020.
10X Genomics, Inc. CG000209 Rev D. Chromium Next GEM Single Cell ATAC Reagent Kits v1.1 User Guide. 2020.
10X Genomics, Inc. CG000239 Rev B. Visium Spatial Gene Expression Reagent Kits User Guide. 2020.
10X Genomics, Inc. CG00026. Chromium Single Cell 3' Reagent Kit User Guide. 2016.
10X Genomics, Inc. LIT00003 Rev B Chromium Genome Solution Application Note. 2017.
Co-pending U.S. Appl. No. 16/708,214, filed Dec. 9, 2019.
Co-pending U.S. Appl. No. 16/737,762, filed Jan. 8, 2020.
Co-pending U.S. Appl. No. 16/737,770, filed Jan. 8, 2020.
Co-pending U.S. Appl. No. 16/789,273, filed Feb. 12, 2020.
Co-pending U.S. Appl. No. 16/789,287, filed Feb. 12, 2020.
Co-pending U.S. Appl. No. 16/800,450, filed Feb. 25, 2020.
Co-pending U.S. Appl. No. 16/814,908, filed Mar. 10, 2020.
PCT/US2020/017785 Application filed on Feb. 11, 2020 by Ziraldo, Solongo B. et al.

(56) References Cited

OTHER PUBLICATIONS

PCT/US2020/017789 Application filed on Feb. 11, 2020 by Belhocine, Zahara Kamila et al.
Biles et al., Low-fidelity Pyrococcus furiosus DNA polymerase mutants useful in error-prone PCR, Nucleic Acids Research, 2004, vol. 32, No. 22 e176, Published online Dec. 15, 2004.
Christian et al., Targeting DNA Double-Strand Breaks with TAL Effector Nucleases, Genetics 186: 757-761 (Oct. 2010).
Co-pending U.S. Appl. No. 17/014,909, inventor Giresi; Paul, filed Sep. 8, 2020.
Co-pending U.S. Appl. No. 17/148,942, inventors McDermott; Geoffrey et al., filed Jan. 14, 2021.
Co-pending U.S. Appl. No. 17/166,982, inventors McDermott; Geoffrey et al., filed Feb. 3, 2021.
Co-pending U.S. Appl. No. 17/175,542, inventors Maheshwari; Arundhati Shamoni et al., filed Feb. 12, 2021.
Co-pending U.S. Appl. No. 17/220,303, inventor Walter; Dagmar, filed Apr. 1, 2021.
Co-pending U.S. Appl. No. 17/381,612, inventor Martinez; Luigi Jhon Alvarado, filed Jul. 21, 2021.
Co-pending U.S. Appl. No. 17/499,039, inventors Pfeiffer; Katherine et al., filed Oct. 12, 2021.
Co-pending U.S. Appl. No. 17/512,241, inventors Hill; Andrew John et al., filed Oct. 27, 2021.
Co-pending U.S. Appl. No. 17/522,741, inventors Zheng; Xinying et al., filed Nov. 9, 2021.
Hockemeyer et al., Genetic engineering of human ES and iPS cells using TALE nucleases, Nat Biotechnol.;29(8): 731-734; available in PMC Feb. 1, 2012.
Miller et al. An improved zinc-finger nuclease architecture for highly specific genome editing, Nature Biotechnology, vol. 25 No. 7; pp. 778-785; Published online Jul. 1, 2007.
Porteus et al., Chimeric Nucleases and Gene Targeting GFP Gene Targeting System, Science. May 2, 2003; vol. 300 (5620):763.
Ran et al., Genome engineering using the CRISPR-Cas9 system, Nature Protocols, vol. 8 No. 11; pp. 2281-2308; Published online Oct. 24, 2013.
Wood et al., Targeted Genome Editing Across Species Using ZFNs and TALENs, Science, Jul. 15, 2011; 333 (6040): 307.
Zhang et al., Efficient construction of sequence-specific TAL effectors for modulating mammalian transcription. Nature Biotechnology, 29(2):149-153; Published online Jan. 19, 2011.
Zhang et al., Programmable Sequence-Specific Transcriptional Regulation of Mammalian Genome Using Designer TAL Effectors, Nat Biotechnol. Feb. 2011 ; 29(2): 149-153.

\* cited by examiner

```
┌─────────────────────────────┐
│   Genes expressed as mRNA   │
│      molecules by a cell    │
│             202             │
└─────────────────────────────┘

┌─────────────────────────────┐
│ Individual mRNA molecules tagged │
│   with transformable tagging     │
│            sequence              │
│              204                 │
└─────────────────────────────┘

┌─────────────────────────────┐
│ Transformable tagging sequence   │
│      transformed to create       │
│ diverse/"unique tagging sequences│
│  such that mRNA molecule → cDNA  │
│    molecule with "unique" tag    │
│              206                 │
└─────────────────────────────┘

┌─────────────────────────────┐
│  Uniquely tagged cDNA molecules  │
│            amplified             │
│              208                 │
└─────────────────────────────┘

┌─────────────────────────────┐
│ Amplified cDNA molecules and tags│
│            sequenced             │
│              210                 │
└─────────────────────────────┘

┌─────────────────────────────┐
│ Gene copies with different/unique│
│  tag sequences counted to assess │
│     expression level of genes    │
│              212                 │
└─────────────────────────────┘
```

Figure 2

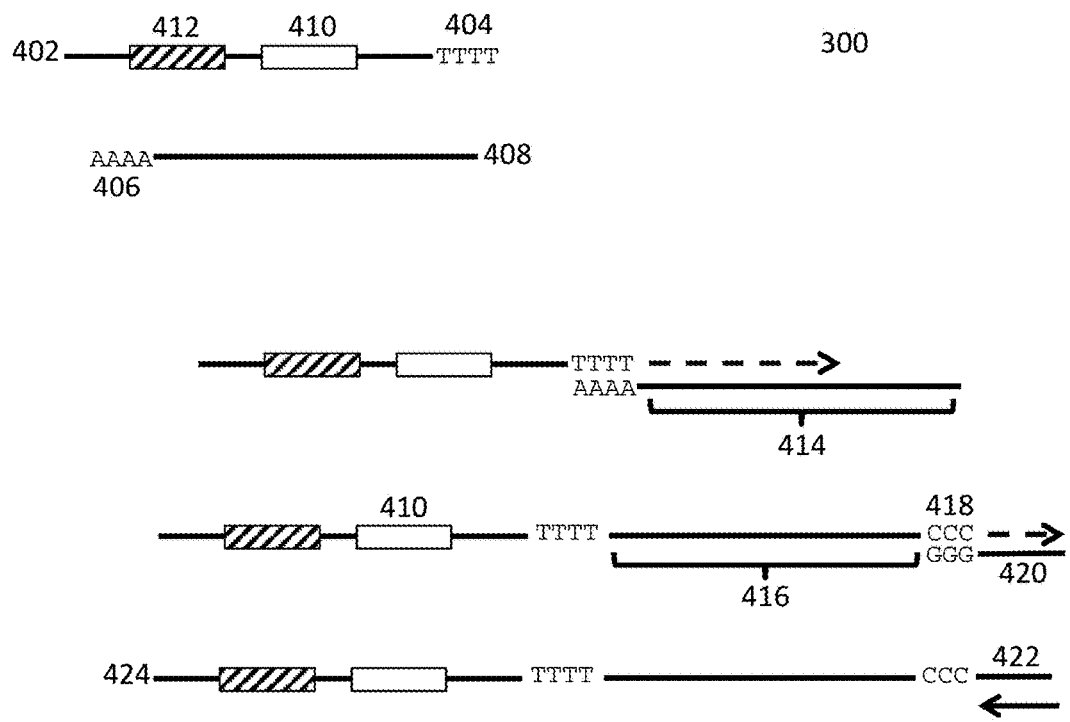
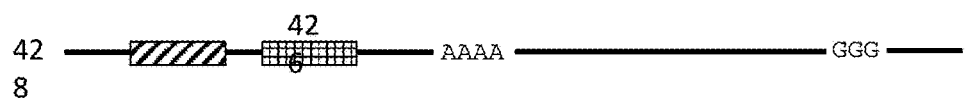
Non wobble base replicate enriched or purified away from Oligos with wobble bases and amplified/sequenced
Figure 4

SYSTEMS AND METHODS FOR NUCLEIC ACID PROCESSING USING DEGENERATE NUCLEOTIDES

CROSS-REFERENCE

This application is a continuation-in-part of U.S. application Ser. No. 15/355,542, filed Nov. 18, 2016, which claims priority to U.S. Provisional Application No. 62/257,438, filed Nov. 19, 2015, which applications are entirely incorporated herein by reference.

BACKGROUND

The field of life sciences has experienced dramatic advancement over the last two decades. From the broad commercialization of products that derive from recombinant deoxyribonucleic acid (DNA) technology, to the simplification of research, development and diagnostics, enabled by the invention and deployment of critical research tools, such as the polymerase chain reaction (PCR), nucleic acid array technologies, robust nucleic acid sequencing technologies, and more recently, the development and commercialization of high throughput next generation sequencing technologies. All of these improvements have combined to advance the fields of biological research, medicine, diagnostics, agricultural biotechnology, and myriad other related fields by leaps and bounds.

Analysis of chemical reactions relies upon the ability to measure, quantify and track the consumption, production, transition and transformation of the various reactants and products involved in those reactions. While in some cases, the reactants and their products are themselves, readily identifiable and measurable, in many cases the analysis benefits from the use of tagging or labeling moieties that are coupled to the reactants and/or products to facilitate their measurement and/or identification.

In some cases, labeling or tagging moieties include more readily identifiable or detectable groups, molecules or chemical moieties. These can include such compositions as fluorescent chemicals, charged chemical groups, affinity binding groups, and in some cases encoded molecules or barcodes that include variable amounts of information within their structure. Examples of particularly useful barcode molecules include, for example, nucleic acid barcodes or tags that can be read out using any of a variety of sequence identification techniques, e.g., nucleic acid sequencing, probe hybridization based assays, and the like.

Barcoding strategies have been applied to a number of tagging and identification strategies. For example, in some cases, step wise building of oligonucleotides on solid supports, e.g., beads, has been used as an indicator of specific chemical synthesis operations in the creation of libraries of molecules on those solid supports, e.g., in a stochastic/combinatorial synthesis process, where the building blocks of the oligonucleotide each reflect a specific chemical synthesis operation to which a given solid support has been exposed (See, e.g., U.S. Pat. No. 5,708,153). By reading out the sequence of added nucleotides on a given solid support, one can identify the synthetic operations and their order, to identify the compound synthesized on that particular solid support.

In still other cases, barcode oligonucleotides have been used in sequencing processes to append pre-synthesized oligonucleotides of known sequence to sequencing libraries created from different samples, such that each different sample has a unique barcode oligonucleotide that is attached to and read out with the sequence of the nucleic acids from that sample. This may allow the pooled analysis of multiple samples, where the resulting sequence information from the pool can be later attributed back to its starting sample.

In another sequencing application, oligonucleotide barcodes have been used in ultra high throughput partitioning systems, to co-partition long fragments of sample nucleic acids along with barcode carrying particles, where the barcodes on an individual particle are identical, but where libraries of particles represent a diverse barcode library. The barcodes are then coupled to sub-segments of the long starting fragments, such that within a given partition, all of the sub-segments of each long fragment bear the same barcode sequence. When the sub-segments are sequenced using, e.g., short-read sequencing systems, one can attribute sub-segments that have the same barcode sequence to the same starting long molecule. This allows retention of long-range sequence context of short sequence reads by virtue of the included barcode sequence (See, e.g., Published U.S. Patent Application Publication No. 2014-0378345, the full disclosure of which is incorporated herein by reference in its entirety for all purposes).

In still other cases, large numbers of diverse barcodes may be introduced into contact with collections of sample molecules, such that the molecules within the collection are each coupled to a different barcode molecule, allowing attribution of a sequence to a specific starting molecule, regardless of how that molecule is amplified, replicated etc., before it is identified. Where samples include multiple copies of the same type of molecule, e.g., the same nucleic acid, sequencing of the underlying molecules as well as the different barcode attached to each molecule may allow one to count how many individual molecules were present at the time of tagging, allowing counting of those starting molecules, e.g., for messenger ribonucleic acid (mRNA) expression analysis, or the like.

SUMMARY

Recognized herein are limitations associated with barcoding strategies currently available. For example, for all of the barcoding strategies described above, an underlying premise is the requirement of large numbers of diverse oligonucleotide barcodes, allowing one to distinguish between large numbers of different results, e.g., samples, partitions, molecules, etc. Preparing, manufacturing and allocating these diverse libraries of molecules across large numbers of samples can prove to be challenging in a number of cases.

The present disclosure provides a dramatic improvement to this approach that can also impart efficiency, cost and other savings to the overall process. The devices, methods and systems of the present invention provide solutions to these and other challenges of the life sciences and other fields.

Provided herein are compositions, systems and methods for tagging molecular events, reactions, species, etc., but without the need for complex, highly diverse libraries of tagging molecules. In particular, provided are tagging moieties that can have a smaller number, a few, or even a single original "tagging" structure that may be transformed or transformable, in situ, into a collection of larger numbers of unique tagging or "barcode" moieties.

In an aspect, the present disclosure provides a method of differentially tagging individual members of a plurality of molecular species, comprising attaching a first tagging moiety to each of a plurality of discrete molecular species, the first tagging moiety comprising a transformable tagging component; and transforming the transformable tagging component attached to each of the plurality of discrete molecules to a transformed tagging component, to distinctly tag a plurality of different members of the plurality of molecular species with different transformed tagging components.

In some embodiments, the plurality of discrete molecular species comprises a plurality of discrete nucleic acid sequences; the tagging moiety comprises an oligonucleotide segment; and the tagging component comprises a transformable oligonucleotide sequence.

In some embodiments, the transformable oligonucleotide sequence comprises one or more transformable nucleotides. In some embodiments, the one or more transformable nucleotides comprise degenerate nucleotides. In some embodiments, the one or more of the one or more transformable nucleotides comprises 2-way degeneracy. In some embodiments, the one or more of the one or more transformable nucleotides comprises 3-way degeneracy. In some embodiments, the one or more of the one or more transformable nucleotides comprises 4-way degeneracy.

In some embodiments, the one or more transformable nucleotides are selected from the group of inosine, deoxyinosine, deoxyxanthine, 2'-deoxynebularine, 2'-deoxyguanosine, 5-nitroindole, 3-nitroindole, N6-methoxy-2,6-diaminopurine, 6H,8H-3,4-dihydropyrimido[4,5-c][1,2]oxazin-7-one, and the non-deoxy (or ribo) versions of each of the foregoing. In some embodiments, the transformable oligonucleotide sequence comprises from 1 to 20 transformable nucleotides.

In some embodiments, the tagging moiety further comprises one or more additional oligonucleotide segments. In some embodiments, the one or more additional oligonucleotide segments are selected from primer sequence segments, hybridization sequence segments, ligation sequence segments, sequencer surface attachment segments, and barcode sequence segments. In some embodiments, the one or more additional oligonucleotide sequences comprises a primer sequence selected from a random primer sequence and a sequencing primer. In some embodiments, the one or more additional oligonucleotide sequences comprises a hybridization sequence. In some embodiments, the hybridization sequence comprises a poly-T sequence.

In some embodiments, the method further comprises partitioning the tagging moieties with a sample comprising nucleic acids to be analyzed prior to the attaching, and wherein the attaching comprises attaching the tagging moieties to the nucleic acids to be analyzed.

In some embodiments, the tagging moieties comprise a poly-T sequence segment, and the nucleic acids to be analyzed comprise mRNA molecules.

In some embodiments, the partitioning comprises partitioning an individual cell with the tagging moieties into a partition, and wherein the nucleic acids to be analyzed are contained within the individual cell and wherein prior to the attaching, the individual cell is lysed to release the nucleic acids to be analyzed into the partition.

In some embodiments, the transformable oligonucleotide sequence segment comprises a target sequence for a sequence substitution system. In some embodiments, the sequence substitution system comprises a CRISPR enzyme system, and the target sequence comprises a target sequence for a targeting oligonucleotide.

In some embodiments, the transforming of the method is random or semi-random.

In another aspect, the present disclosure provides a method of analyzing nucleic acid molecules, comprising attaching an oligonucleotide segment to a target oligonucleotide molecule to generate a tagged oligonucleotide, wherein the oligonucleotide comprises a region that comprises a plurality of variable complement nucleotides; replicating the tagged oligonucleotide to generate a replicated tagged oligonucleotide, whereby replication generates a random or partially random replicate of the region; and analyzing the replicated tagged oligonucleotide, including the random or partially random replicate, to identify the target oligonucleotide molecule.

In some embodiments, the region comprises from 2 to 20 variable complement nucleotides. In some embodiments, the region comprises two or more contiguous variable complement nucleotides.

In some embodiments, the two or more of the variable complement nucleotides are separated from each other by one or more non-variable complement nucleotides.

In some embodiments, the region comprises from 4 to 10 variable complement nucleotides.

In some embodiments, the first oligonucleotide comprises an additional region that comprises a plurality of variable complement nucleotides.

In another aspect, the present disclosure provides an oligonucleotide composition, comprising an oligonucleotide that comprises a first region and a second region, wherein the second region comprises a fixed sequence comprising a plurality of variable complement nucleotides, which plurality of variable complement nucleotides is transformable to yield a distinct molecular tag.

In some embodiments, the first region comprises an attachment sequence for attachment of the oligonucleotide to a nucleic acid molecule to be analyzed. In some embodiments, wherein the attachment sequence comprises a primer sequence. In some embodiments, the attachment sequence comprises a poly-T sequence.

In some embodiments, the first region comprises a barcode sequence. In some embodiments, the first region comprises a surface attachment sequence.

In some embodiments, the second region comprises a plurality of variable complement nucleotides and one or more non-variable complement nucleotides.

In another aspect, the present disclosure presents a method of quantifying nucleic acid molecules in a population of identical nucleic acid molecules, comprising mutating the population of identical nucleic acid molecules at an expected mutagenesis rate to create a population of different mutated nucleic acids; sequencing the distinct mutated nucleic acid molecules; and computing a quantification of the nucleic acid molecules in the population of identical nucleic acid molecules based upon a number of different mutated nucleic acid molecules.

In some embodiments, the computing comprises quantifying the nucleic acid molecules in the population of identical nucleic acid molecules based upon the number of different mutated nucleic acid molecules and the mutagenesis rate.

In some embodiments, the sequencing comprises generate sequencing reads from the distinct mutated nucleic acid molecules.

In some embodiments, the computing comprises computing a comparison of the sequencing reads to quantify the nucleic acid molecules in the population of identical nucleic acid molecules.

In another aspect, the present disclosure presents a method of differentiating amplification products from two or more identical nucleic acid molecules, comprising subjecting the two or more nucleic acid molecules to mutagenesis to produce two or more mutated nucleic acid molecules; amplifying the two or more mutated nucleic acid molecules to generate amplified mutated nucleic acid products; and sequencing the amplified mutated nucleic acid products.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

FIG. 2 provides a high level flow chart of an example tagging process of the present disclosure;

FIG. 4 provides a schematic illustration of a tagging process of the present disclosure for use in, e.g., the quantification of messenger ribonucleic acid (mRNA) expressed from genes within cells.

DETAILED DESCRIPTION

Figure 1:
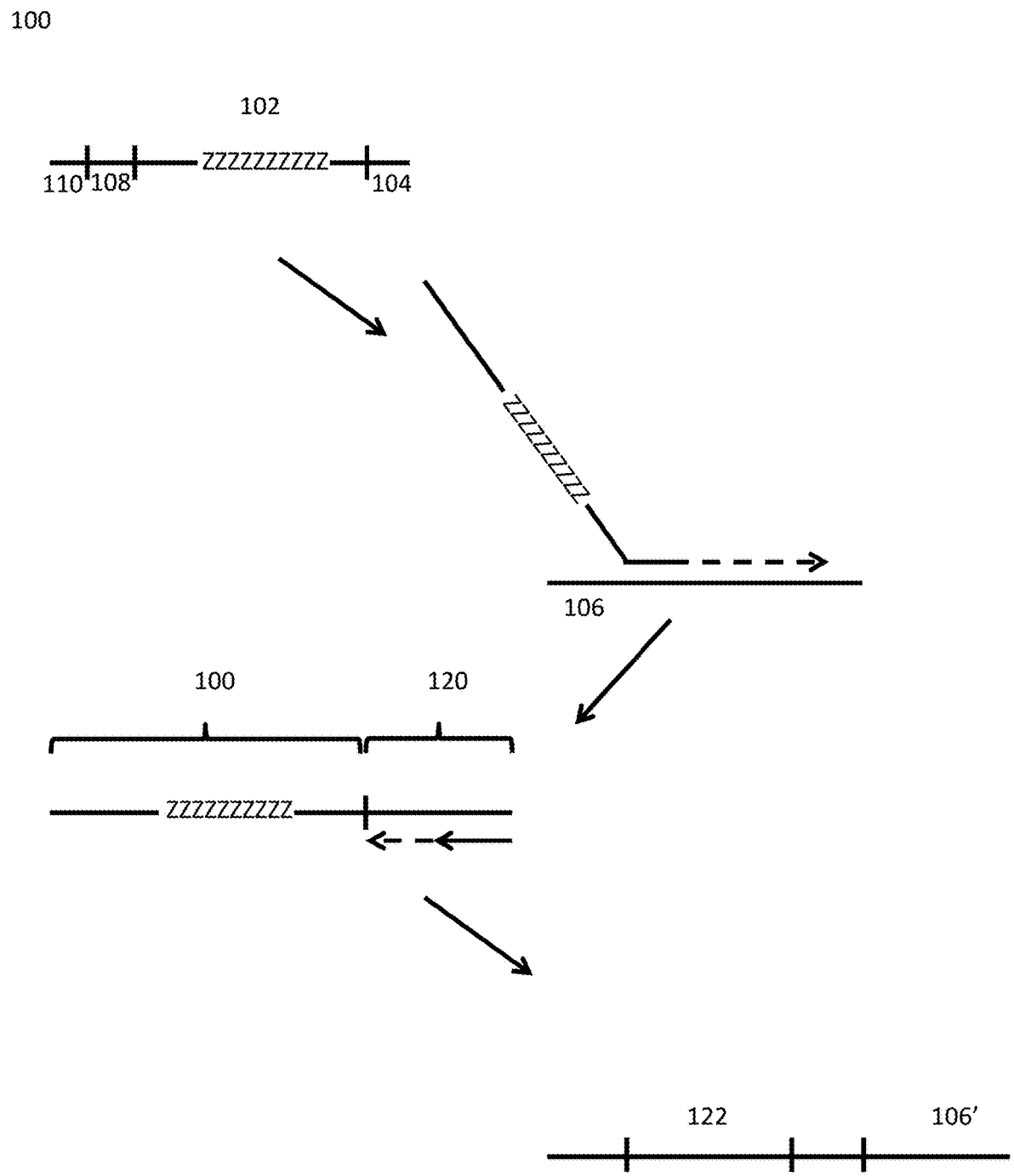
FIG. 1 provides a schematic illustration of a tagging construct and its implementation, in accordance with the present disclosure.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

The term "sample," as used herein, generally refers to a biological tissue, cells or fluid. Such sample may include, but is not limited to, sputum, blood (e.g., whole blood), serum, plasma, blood cells (e.g., white cells), tissue, nipple aspirate, core or fine needle biopsy samples, cell-containing body fluids, free floating nucleic acids, urine, peritoneal fluid, and pleural fluid, or cells there from. A sample may be a cell-free (or cell free) sample. A sample may include one or more cells.

The term "nucleic acid," as used herein, generally refers to a monomeric or polymeric form of nucleotides of any length, either deoxyribonucleotides or ribonucleotides, or analogs or variants thereof. A nucleic acid molecule may include one or more unmodified or modified nucleotides. Nucleic acid may have any three dimensional structure, and may perform any function, known or unknown. The following are non-limiting examples of nucleic acids: ribonucleic acid (RNA), deoxyribonucleic acid (DNA), coding or non-coding regions of a gene or gene fragment, loci (locus) defined from linkage analysis, exons, introns, messenger RNA (mRNA), transfer ribonucleic acid (RNA), ribosomal RNA, short interfering RNA (siRNA), short-hairpin RNA (shRNA), micro-RNA (miRNA), ribozymes, complementary deoxyribonucleic acid (cDNA), recombinant polynucleotides, branched polynucleotides, plasmids, vectors, isolated DNA of any sequence, isolated RNA of any sequence, nucleic acid probes, and primers. Nucleic acid may comprise one or more modified nucleotides, such as methylated nucleotides and nucleotide analogs, such as peptide nucleic acid (PNA), Morpholino and locked nucleic acid (LNA), glycol nucleic acid (GNA), threose nucleic acid (TNA), 2'-fluoro, 2'-OMe, and phosphorothiolated DNA. A nucleic acid may include one or more subunits selected from adenosine (A), cytosine (C), guanine (G), thymine (T) and uracil (U), or variants thereof. In some examples, a nucleic acid is DNA or RNA, or derivatives thereof. A nucleic acid may be single-stranded or double stranded. A nucleic acid may be circular.

The term "nucleotide," as used herein, generally refers to a nucleic acid subunit, which may include A, C, G, T or U, or variants or analogs thereof. A nucleotide can include any subunit that can be incorporated into a growing nucleic acid strand. Such subunit can be an A, C, G, T, or U, or any other subunit that is specific to one or more complementary A, C, G, T or U, or complementary to a purine (i.e., A or G, or variant or analogs thereof) or a pyrimidine (i.e., C, T or U, or variant or analogs thereof). A subunit can enable individual nucleic acid bases or groups of bases (e.g., AA, TA, AT, GC, CG, CT, TC, GT, TG, AC, CA, or uracil-counterparts thereof) to be resolved.

General

Transformable tagging groups as described herein may be employed in a variety of useful contexts. For example, they may be used to impart a level of tag diversity, in situ, without requiring that level of diversity in the originating tag reagent. Additionally, they may be employed as indicators of replication cycles, as random differentiation tags, as part of a process for creating highly diverse barcode libraries, as unique molecular identifier molecules in certain types of analyses, such as molecular counting applications (e.g., for expression analysis, to increase confidence in variant calls in nucleic acids; e.g., by counting molecules supporting a given allele, and by taking consensus amongst short reads with a common molecular identifier to improve sequencing accuracy, as well as determination of copy number variations), as tracking tags for tracking lineages in populations, e.g., for phylogenetic reconstruction, as indicators of enzyme activity, or indicators of proximity or interaction between multiple molecules. A variety of other uses will be apparent to those of skill in the art upon reading this disclosure.

In an application, these transformable tagging moieties may be employed as individual molecule tags for use in molecular quantitation processes. In many applications, unique molecular identifier tags have been used to tag individual molecules in order to be able to individually identify separate starting molecules in order to quantify them. In an example, it can be desirable to be able to quantify the number of separate messenger ribonucleic acid (mRNA) molecules from a given gene in a cell or other sample, in order to be able to measure the expression levels of that gene, either generally, or in response to some stimulus, e.g., a drug candidate or other environmental stimulus. In this context, discrete copies of mRNA molecules within a cell, that are expressed from a given gene, may be stochastically tagged with different nucleic acid barcode molecules, such that each discrete molecule has a unique identifier sequence attached to it, or a unique molecular identifier ("UMI"). Because each starting mRNA molecule expressed from a given gene now has a UMI sequence attached to it, it can be subjected to rounds of amplification, without losing the information as to the number of starting molecules, e.g., each different UMI attached to mRNA denotes a separate starting molecule. Amplification allows for greatly simplified detection, e.g., using nucleic acid arrays that target the genes of interest or the UMIs, nucleic acid sequencing, or other approaches. Following amplification, detection of the different UMIs present allows the inference of the number of starting mRNA molecules for a given gene, and thus an inference of expression of that gene. Examples of this type of use of UMIs are described in, e.g., "Counting Absolute Numbers of Molecules Using Unique Molecular Identifiers", Kivioja, et al., Nature Methods 9, 72-74 (2012), the full disclosure of which is incorporated herein by reference in its entirety for all purposes.

While useful in some contexts, it will be appreciated that these methods may be reserved for samples with relatively small numbers of molecules, as the requisite tagging library may rapidly increase in complexity and cost, as the number of molecules in a sample increase. Restated, as the number of molecules to be counted increases, it may result in a necessary and substantial increase in the number of different tagging moieties that may be required to be applied to the sample, in order to get unique molecular tagging. Likewise, as the number of different genes to be analyzed increases, it increases the required complexity of the UMI library. Moreover, biochemistries for the creation, ligation or other attachment, replication, etc. of these diverse libraries cannot be optimized for any particular sequence, but may be optimized for the average sequence, which will typically result in optimization for none of the actual sequences used.

As described herein, however, a relatively simple and constant tagging structure may be used that incorporates transformable moieties, as described above, within the tagging moiety in order to impart diversity, in situ, to the tagged molecules. In particular, one may employ a tagging moiety that has a single, but transformable tagging moiety, where subsequent processing of tagged molecules will transform the tagging molecule in a random or semi-random way, to impart diversity to the tagging groups in a sample, where that level of diversity did not exist originally. This allows one to use a small number, a few or even a single transformable tagging moiety in an analysis in place of much larger numbers of unique barcode molecules required by prior processes, as the diversity required for a given analysis will be introduced upon random or semi-random transformation of the tag.

In the context of the expression analysis example, above, in place of the diverse library of nucleic acid UMIs that are individually and stochastically attached to separate mRNA molecules, one may attach a single, few, or relatively small number of transformable tagging moieties to the different mRNAs. Following a single round of replication, each copy of mRNA for a given gene may be replicated with a random or semi-random sequence tag attached, that by virtue of the randomness or semi-randomness of the replication process for the tag, may yield a differently tagged replicate for each starting molecule. By then detecting and counting the number of different transformed tagging moieties, one may infer the number of starting mRNA molecules.

Transformable Tagging Moieties

The present disclosure provides "tagging" moieties that include transformable elements that may be converted into a desired tagging structure after they are associated with the component, which they are intended to tag. In some cases, these transformable structures may possess a common structure, but are transformed into a diverse set of structures after the transformation process, e.g., where a population of tags having a single structure is transformed into a diverse population of different structures. In some cases, these transformable groups are transformed into random or semi-random resultant moieties to impart diversity to the tagged molecules which can be identified and used in the characterization of, e.g., a reaction, its reactants and/or its products.

While specific examples of transformable tagging moieties are described in terms on nucleic acids, polynucleotides, etc., it will be appreciated that other transformable tagging moieties may be employed. For example, transformable moieties may comprise nucleic acids (e.g., nucleotides, oligonucleotides, polynucleotides, including ribonucleotides and deoxyribonucleotides, as well as analogs of these, such as dideoxy ribonucleotides, degenerate nucleotides, etc.), polypeptides (e.g., proteins, enzymes, polypeptides, oligopeptides, etc.), carbohydrates (e.g., dextrans, starches, celluloses, etc.), organic compounds, fluorophores, chromophores, colloidal elements, particles, beads, or the like, where a first structure may be transformed into one or more second structures upon implementation of a process operation, in order to gain diversity of tagging moieties in a reaction.

In an example, a transformable moiety may include a transformable oligonucleotide sequence, where during replication, translation, transcription, or other transformation processes, the nucleotides of such sequence (also referred to herein as "bases" for simplicity) in the sequence are transformable, in situ, to varied or variable resulting species. A variety of different mechanisms may be used to transform nucleotides in a sequence, in situ, including, for example, the use of degenerate bases, e.g., bases for which complementary base pairing may vary, sequence segment based transformation, e.g., removing and replacing sequence segments, as well as chemical transformations of individual bases or sequences of bases, e.g., oxidative deamination of bases, or other chemical modifications (e.g., treatment with nitrous acid or alkylating agents), exposure to ionizing radiation, treatment with enzymes that modify bases (e.g., adenosine deaminase, cytosine deaminase, xanthine oxidase, editosomes), that change base pairing or processes that cause template driven or non-template drive insertion or addition, such as M-MLV reverse transcriptases, terminal deoxynucleotidyl transferases, or transposons that catalyze their own insertion.

In certain cases, the transformable nucleotides may include nucleotides that are subject to random or semi-random "complement" incorporation, which nucleotides, or bases, may also be referred to herein as variable complement nucleotides or bases. In particular, during oligonucleotide replication, transcription or translation, faithful processing by the involved enzymes or enzyme systems typically incorporates a single type of complementary building block in response to encountering a given nucleotide or set of nucleotides. For example, template driven, polymerase mediated nucleic acid replication using typical faithful DNA polymerase enzymes, e.g., a DNA polymerase replicating a given DNA strand, when it encounters one type of nucleotide, will typically incorporate a single specific type of complementary nucleotide. For example, when encountering a purine adenosyl (A) or guanidyl (G) nucleotide in the sequence, a polymerase will typically incorporate a pyrimidine thymidyl (T) or cytosyl (C) nucleotide as the complementary base in the sequence, respectively, and vice versa. Thus, a typical barcode sequence made up of these bases may typically be replicated into the same complementary structure substantially every time by the faithful polymerase enzyme. In accordance with some aspects of the present disclosure, however, a barcode segment may include one or more nucleotides that are capable of having random or semi-random complements, such that when replicated, they produce random or semi-random replicate sequences in response. As will be appreciated, random incorporation may likewise be driven through the use of a lower fidelity polymerase enzymes toward conventional bases, or non-proofreading enzymes, e.g., having substitution rates of greater than 0.1%, and in some cases greater than 1%, greater than 5% or even higher. Examples of such low fidelity polymerases include, e.g., Family Y polymerases, translesion synthesis polymerases, *Escherichia coli* polymerases IV and V, human polymerases; ζ, π, τ, κ and Rev1, as well as modified versions of polymerases having reduced or no proofreading capability, such as phi29 mutant enzymes, phi29 N62D and other non-proofreading mutants (e.g., as described in Korlach et al., Methods in Enzymology, Real-Time DNA Sequencing from Single Polymerase Molecules, (2010) 472:431-455), low-fidelity mutants of pfu-Pol (see, e.g., Biles et al., Nucl. Acids Res. 32(22):e176 2004), viral polymerases such as DNA Polymerase X (Pol X) from African Swine Fever Virus (ASFV), Such polymerases may be used alone or in combination with transformable bases as described elsewhere herein, or may be used in conjunction with particular sequence motifs for which these polymerases demonstrate higher base substitution rates. In some cases, a single type of polymerase may be used in achieving the transformation of the tagging sequence. Conversely, in other cases, mixes of different polymerase enzymes having different responses to different degenerate bases, may be combined in single reaction mixture to increase diversity or otherwise better control the transformation process.

A variety of nucleotide or nucleotide like moieties have been described that have random or semi-random complements when replicated in polymerase reactions, e.g., during replication, they may be complemented with two or more different nucleotides in the produced or "replicate" strand. For ease of discussion, these bases are referred to herein as degenerate bases. For example, a number of bases are able to interact with a polymerase in a way which will be unbiased enough to at least provide two-way degeneracy in replicating at that base, i.e., able to incorporate two or more different nucleotides in response to and as a "complement" to such bases. In some cases, bases that result in polymerase incorporation at a level of at least 2-way, at least 3-way, or even 4-way degeneracy may be used. Generally, as used herein, degeneracy generally refers to bases that under particular reaction conditions, e.g., using a particular polymerase with particular nucleotide, buffer, and salt concentrations, etc., will exhibit unbiased incorporation, e.g., will incorporate a different nucleotide in response to a degenerate base, in at least 1% of the instances in which it encounters such degenerate base, at least 5% of the instances, in some cases, at least 10% of the time, in some cases a least 20% of the time, in some cases at least 30% of the time, in some cases at least 40% of the time, and in some cases, at least 50% of the time. For example, and solely for ease of discussion, a transformable nucleotide may exhibit two way degeneracy if it results in different base incorporations, e.g., at least 5% of the time, e.g., if it incorporates an A 5% of the time, and a G the other 95% of the time.

As alluded to above, in some cases, concentrations of various nucleotides within the polymerization reaction mixture may be adjusted to provide a desired degeneracy rate in a given reaction. For example, to even out incorporation of different bases, one may adjust their relative concentrations to increase incorporation rate of one while decreasing the relative incorporation rate of another in response to a given transformable or degenerate base. As such, one may provide even two way, three way or four way degeneracy at a given degenerate base by providing the various nucleotide reagents at concentrations that yield an equivalent incorporation rate of each at the particular degenerate base.

As will be appreciated, bases that result in "complement" incorporation that exhibits the above-described degeneracy will be characterized as being random or semi-random. For example, in some cases, a defined bias toward a subset of complement bases, e.g., only purines, or only pyrimidines, may be identified as being semi-random, where complete indiscriminate complement paring of a given base may be viewed as being completely random.

Examples of such transformable nucleotides may include, e.g., inosine, deoxyinosine, deoxyxanthine, 2'-deoxynebularine, 2'-deoxyguanosine, 5-nitroindole, 3-nitroindole, N6-methoxy-2,6-diaminopurine, 6H,8H-3,4-dihydropyrimido[4,5-c][1,2]oxazin-7-one, and the non-deoxy (or ribo) versions of each of the foregoing. For these bases, one may provide for a variety of incorporation patterns using one or more of these bases as transformable bases within a transformable tagging sequence, depending upon the transformable bases used. For example, some transformable bases, such as inosine, while displaying levels of degeneracy, may nonetheless display a stronger preference to complement with, and therefor drive the incorporation of one type of nucleotide, e.g., cytosine nucleotide (C). Other transformable bases, like 5-nitroindole, may show more balanced 4-way degeneracy, e.g., an ability to incorporate any of the four natural bases, e.g., AGCT, in response. In another example, deoxyxanthine, while displaying 4-way degeneracy, in some cases displays a stronger preference for complementing with pyrimidine nucleotides, e.g., T or C.

A tagging or barcode sequence including one or more of these degenerate bases may be employed by appending the tagging sequence segment to a target nucleic acid or nucleic acid fragment of interest. Upon polymerase mediated replication of the target nucleic acid, the tag group will also be "replicated", but that replication may incorporate random or semi-random complement bases to the degenerate base positions to create a unique or semi-unique tag appended to the replicate molecule. As a result, a single sequence of degenerate bases can give rise to a number, and potentially a large number of different tag sequences upon polymerase replication.

As will be appreciated, the transformable oligonucleotide tagging sequences may include degenerate bases in addition to non-degenerate bases, or they may include all degenerate bases. Likewise, the degenerate bases included may have two way degeneracy, three-way degeneracy or four-way degeneracy, and/or may have certain preferences despite their level of degeneracy. In some cases, degenerate bases may be interspersed with non-degenerate bases, or two-way degenerate bases may be interspersed with three and/or 4 way degenerate bases in random or even known or predetermined patterns. Use of known or predetermined patterns may permit the ready identification of the tag sequences by virtue of their reflection of a known or predetermined pattern reflective of the pattern of degenerate bases and/or non-degenerate bases included.

In some cases, and depending upon a desired level of possible diversity, the number of degenerate bases in a given tagging sequence may vary from 1 to 100 or more, from 1 to 20 transformable bases, from 1 to 10 transformable bases, from 1 to 5 transformable bases, or any intermediate number of transformable bases within any of the foregoing ranges.

Moreover, these transformable bases may, as noted previously, be contiguous within a sequence segment, or they may be interspersed with non-degenerate bases. Such interspersed bases may separate individual transformable bases from other transformable bases within the tagging sequence, or they may separate pairs, groups or subsets of transformable bases from other individual, pairs, groups or subsets of transformable bases. These interspersed transformable bases may, likewise, be present is individual bases in the sequence, or as contiguous pairs, groups or subsets of non-transformable bases in the tagging sequence.

As will be appreciated, one may select the level of potential diversity for a transformable tagging sequence through selection of the number of degenerate or transformable bases in a tagging sequence, and the level of degeneracy for each such base. Moreover, as discussed above, one can introduce a level of additional diversity by providing sets of transformable tagging segments with varying sequences of transformable nucleotides, e.g., by shuffling the order to the degenerate bases used in a library of tagging molecules. Such selection can be motivated by any of a number of requirements or desires, including, the level of diversity required or desired for any given application, e.g., the number of expectant molecules to be tagged in a molecular counting application, as well as the desire to be able to identify tagging sequences from a higher level signature, e.g., resulting from their semi randomness. For example, one may select the transformable bases in a tagging sequence to reflect a general pattern of resulting sequences, e.g., localizing purine or pyrimidine specific transformable bases at certain positions, as well as non-degenerate bases interspersed among other transformable bases. By incorporating patterns of semi-random transformable bases or overall sequences, one may be able to better identify sequences that more likely result from the tagging sequence.

In other cases, the transformable tagging moiety may include a segment that is transformed in whole, as opposed to on a building block by building block basis. For example, in some cases, an original tagging moiety may be provided that presents a target for insertion of a replacement sequence segment that yields a desired level of diversity while starting from a common original tagging segment. An example of such an approach may include the use of a targeted mutagenesis mechanism where a transformable sequence segment may be transformed (e.g., altered or replaced, in whole or in part). For example, a tagging sequence segment may form the basis of a target sequence for a targeted sequence replacement system. For example, a transformable tagging sequence segment may be targeted using, e.g., a guide RNA associated with a CRISPR associated RNA guided DNA endonuclease enzyme, such as Cas9, that is able to target a specific sequence through the guide RNA, and excise that sequence (See, e.g., Genome Engineering Using the CRISPR-Cas9 System, Ran, et al., Nature Protocol, (2013), 8(11):2281-2308). Once excised, replacement sequence segments may be readily inserted by using, e.g., complementary flanking regions that allow ligation of the new sequence segment at the point of excision of the prior transformable sequence segment, using, e.g., conventional ligation biochemistries or employing, e.g., non-homologous end joining (NHEJ) or homology-directed repair (HDR). As will be appreciated, a variety of other targeted editing nucleases may be used in a similar fashion, e.g., including for example, zinc finger nucleases (ZFNs), and transcription activator-like effector nucleases (TALENs), see, e.g., Porteus MH, Baltimore D. Chimeric nucleases stimulate gene targeting in human cells. Science. 2003; 300:763; Miller J C, et al. An improved zinc-finger nuclease architecture for highly specific genome editing. Nat. Biotechnol. 2007; 25:778-785; Sander J D, et al. Selection-free zinc-finger-nuclease engineering by context-dependent assembly (CoDA). Nat. Methods. 2011; 8:67-69; Wood A J, et al. Targeted genome editing across species using ZFNs and TALENs. Science. 2011; 333:307; Christian M, et al. Targeting DNA double-strand breaks with TAL effector nucleases. Genetics. 2010; 186: 757-761; Zhang F, et al. Efficient construction of sequence-specific TAL effectors for modulating mammalian transcription. Nat. Biotechnol. 2011; 29:149-153; Hockemeyer D, et al. Genetic engineering of human pluripotent cells using TALE nucleases. Nat. Biotechnol. 2011; 29:731-734.

In some cases, a transformable tagging moiety, e.g., a transformable sequence may comprise a sequence that is more susceptible and/or subject to chemical or UV mutagenesis in order to drive transformation of the tagging segment or even transformation of the sequence segment of interest, such that such mutagenesis results in sufficient diversity for a given analysis. For example, if counting identical sequences, one may mutagenize such sequences in a manner that is expected to impact each and every molecule. Subsequent analysis of those sequences, may allow one to determine the number of staring molecules based upon the number of differently mutated sequences. Such mutagenesis may in some cases, again, be targeted using, e.g., targeting or guide oligonucleotide probes, or it may be random, e.g., non-targeted.

Structures

Also provided herein are compositions that include oligonucleotides that comprise as a part of their sequences, the tagging oligonucleotide sequences or segments described elsewhere herein. These compositions may include these oligonucleotides alone, or in conjunction with other components, including without limitation, buffers, salts, reactants, enzymes, sample components, e.g., cells, tissues or other sample constituents, solid supports, such as particles, beads, hydrogel beads, array surfaces, etc.

The tagging moieties described herein may include additional elements within their larger structure, e.g., to impart additional functionality to the tagging moieties. For example, such structures may include additional elements that may provide functions within an application of the tagging moiety or for the resulting tagged reactant.

By way of example, the tagging moieties described may be provided within structures that facilitate their attachment or appending to other reactants. For example, they may include activatable chemical groups that can facilitate chemical coupling with other groups, affinity binding portions, e.g., avidin, streptavidin, biotin, etc., for affinity attachment, or they may include other mechanisms allowing for this coupling.

By way of example, oligonucleotide tagging moieties, as described above, may include additional sequence segments that permit their attachment or appending to other sequence segments, e.g., target sequence segments. As will be appreciated, attachment or appending of a tagging moiety, e.g., a tagging oligonucleotide, to another species, e.g., a target nucleic acid sequence or portion thereof, includes a variety of different attachment or appending approaches. For example, in some cases, attachment of a tagging oligonucleotide to another sequence segment may comprise covalent attachment via, e.g., ligation attachment to a 3' or 5' end of the other sequence segment, or through covalent cross-linking or other side chain attachment to the other sequence segment.

Additionally, attachment may include non-covalent attachment to the other sequence segment, e.g., through affinity coupling, such as through hybridization of a portion of the tagging oligonucleotide to the targeted sequence segment, or through other affinity mechanisms for other molecular species, e.g., through antibody/antigen coupling, avidin or streptavidin/biotin coupling, or through association with specific association groups, e.g., association peptides, and the like.

In still other aspects, attachment of a tagging oligonucleotide may be through the priming and extension of primer sequences that are included within the tagging oligonucleotide structure, such that a complement of the targeted sequence segment is attached to the extended primer/tagging oligonucleotide. As will be appreciated, the tagging oligonucleotide and the sequence segment, when referred to as attached, will interchangeably refer to the complements or replicates of either or both sequence segments. Accordingly, and as will be appreciated, attachment will include both the attachment of a tagging moiety to a sequence segment, as well as attachment of the tagging oligonucleotide to a complement of the sequence segment, as well as attachment of a complement to the original tagging oligonucleotide to a sequence segment, its complement or a further complement of such complement (i.e., a replicate of an original sequence segment).

The additional sequence segments may comprise hybridization probes for attaching to the target sequences by hybridization, or they may include primer sequences that are capable of annealing to the target sequence segments, such that extension of the primer segment replicates a complement to the target sequence into the extension product that includes the tagging sequence, which for purposes of the present disclosure constitutes attachment or appending of the tagging molecule to the target, as used herein.

In some cases, the tagging moieties may include sequence overhangs and/or bridging or splint sequences in order to facilitate ligation or other coupling of the tagging moiety to a given sequence.

Priming or hybridization sequences may be constructed to anneal to specific sequences within a target sequence, or they may be constructed to anneal to random portions of target sequences, e.g., as universal primers, such as random n-mer sequences, such that different primer sequences on different tagging oligonucleotides may prime at different locations within a target sequence.

An example of a tagging oligonucleotide and its use in tagging a segment of a target sequence is illustrated in FIG. 1. As shown, an oligonucleotide 100 includes a tagging segment 102 that comprises one or more degenerate bases (Z) within its sequence. The one or more degenerate bases may be in a given region of the oligonucleotide 100. In some cases, the oligonucleotide 100 includes at least 2, 3, 4, 5, 6, 7, 8, 9, or 10 regions each with one or more degenerate bases. As noted above, although illustrated as including a number of contiguous degenerate bases, the tagging sequence may, in some cases, include one or more non-degenerate bases within its sequence. Likewise, although shown as a 10-mer tagging sequence, or a tagging sequence including 10 degenerate bases, the tagging sequence may be longer or shorter, and include more or fewer degenerate bases, as described elsewhere herein.

The tagging sequence may include at least 2, 3, 4, 5, 6, 7, 8, 9, 10, 20, 30, 40, 50, 60, 70, 80, 90 or 100 degenerate bases. The tagging sequence may include at least 2, 3, 4, 5, 6, 7, 8, 9, 10, 20, 30, 40, 50, 60, 70, 80, 90 or 100 nucleotides.

Oligonucleotide 100 is also shown as including a priming sequence 104 at its 3' terminus, for annealing to and priming replication of a target sample nucleic acid fragment 106. As will be appreciated, this priming sequence may be specific to a sequence within the target sequence of interest, it may be a random priming sequence, e.g., an n-mer, or it may be targeted to a particular type of sequence segment, e.g., to anneal to a poly-adenylated terminus (poly-A tail) of a mRNA molecule, or other common sequence type. Also as shown, oligonucleotide 100 may include additional nucleic acid segments, such as additional barcode segment 108, sequencing primer segment 110, as well as sequencer specific attachment sequences (not shown). For example, the oligonucleotide 100 may include a flow cell sequence for use in massively parallel sequencing (e.g., Illumina sequencing).

As shown, tagging oligonucleotide 100 anneals to a target sequence of interest and is used to prime extension and complementary replication of that target sequence, resulting in the tagging oligonucleotide 100 being appended to the complement replicate segment 120 of the target sequence 106. Upon subsequent replication of tagged segment 102 in tagging oligonucleotide 100, the transformable nature of tagging segment 102 replicates into a random or semi-random sequence segment 122 attached to a copy 106' of the original target sequence segment 106. The resultant random or semi-random segment 122 may be different for different molecules in the sample, despite originating from the same tagging oligonucleotide sequence segment 102 in tagging oligonucleotide 100.

As noted above, a number of other structures may be included along with the transformable tagging sequence segments described above. For example, in some cases, the transformable tagging segments may be included in an oligonucleotide structure along with other tagging or barcoding structures. Examples of particularly useful barcoding oligonucleotides are described in, e.g., Published U.S. Patent Application Publication Nos. 2014/0378345, 2014/0228255, 2015/0376700, 2015/0376605, and 2016/0122817, the full disclosures of which are hereby incorporated herein by reference.

The barcodes can have a variety of structures. In some cases, barcodes are a part of an adapter. Generally, an "adapter" is a structure used to enable attachment of a barcode to a target polynucleotide. An adapter may comprise, for example, a barcode, polynucleotide sequence compatible for ligation with a target polynucleotide, and functional sequences such as primer binding sites and immobilization regions. In some cases, an adapter is a forked adapter.

In some cases, these barcodes may be used to tag sequence segment fragments that have been co-partitioned into, e.g., submicroliter droplets (nanoliter or picoliter scale droplets). Such sequence segments may be derived from solutions of sample nucleic acids or from individual cells that are co-partitioned with the barcodes for tagging. Additionally or alternatively, the additional tagging or barcoding structures may include a separate barcode reflective of the specific sample from which the nucleic acids were derived, in order to allow subsequent differentiation of nucleic acids from different sample on a pooled sequencing run.

In some cases, the tagging oligonucleotides described herein, including any additional sequence segments, may be provided as elements of a larger oligonucleotide library. For example, the tagging oligonucleotide segments are incorporated into barcode oligonucleotide libraries, such as those described in Published U.S. Patent Application Publication No. 2014/0228255, incorporated herein by reference in its entirety for all purposes.

Random methods of polynucleotide synthesis, including random methods of DNA synthesis can be used to generate barcode oligonucleotide libraries. During random DNA synthesis, any combination of A, C, G, and/or T may be added to a coupling operation so that each type of base in the coupling operation is coupled to a subset of the product. If A, C, G, and T are present at equivalent concentrations, approximately one-quarter of the product will incorporate each base. Successive coupling steps, and the random nature of the coupling reaction, enable the generation of $4^n$ possible sequences, where n is the number of bases in the polynucleotide. For example, a library of random polynucleotides of length 6 may have a diversity of $4^6=4,096$ members, while a library of length 10 may have diversity of 1,048,576 members. Therefore, very large and complex libraries can be generated. These random sequences may serve as barcodes. Any suitable synthetic bases may also be used. In some cases, the bases included in each coupling operation may be altered in order to synthesize a preferred product. For example, the number of bases present in each coupling operation may be 1, 2, 3, 4, 5, 6, 7, 8, 9, 10, or more. In some cases, the number of bases present in each coupling operation may be at least 1, 2, 3, 4, 5, 6, 7, 8, 9, 10, or more. In some cases, the number of bases present in each coupling operation may be less than 2, 3, 4, 5, 6, 7, 8, 9, or 10. The concentration of the individual bases may also be altered in order to synthesize the preferred product. For example, any base may be present at a concentration of about 0.1, 0.5, 1, 5, or 10-fold the concentration of another base. In some cases, any base may be present at a concentration of at least about 0.1, 0.5, 1, 5, or 10-fold the concentration of another base. In some cases, any base may be present at a concentration of less than about 0.1, 0.5, 1, 5, or 10-fold the concentration of another base. The length of the random polynucleotide sequence may be any suitable length, depending on the application. In some cases, the length of the random polynucleotide sequence may be 4, 5, 6, 7, 8, 9, 10, 11, 12, 13, 14, 15, 16, 17, 18, 19, 20, or more nucleotides. In some cases, the length of the random polynucleotide sequence may be at least 4, 5, 6, 7, 8, 9, 10, 11, 12, 13, 14, 15, 16, 17, 18, 19, 20, or more nucleotides. In some cases, the length of the random polynucleotide sequence may be less than 4, 5, 6, 7, 8, 9, 10, 11, 12, 13, 14, 15, 16, 17, 18, 19, or 20 nucleotides. In some cases, the library is defined by the number of members. In some cases, a library may comprise about 256, 1024, 4096, 16384, 65536, 262144, 1048576, 4194304, 16777216, 67108864, 268435456, 1073741824, 4294967296, 17179869184, 68719476736, $2.74878*10^{11}$, or $1.09951*10^{12}$ members. In some cases, a library may comprise at least about 256, 1024, 4096, 16384, 65536, 262144, 1048576, 4194304, 16777216, 67108864, 268435456, 1073741824, 4294967296, 17179869184, 68719476736, $2.74878*10$, or $1.09951*10^{12}$ members. In some cases, a library may comprise less than about 256, 1024, 4096, 16384, 65536, 262144, 1048576, 4194304, 16777216, 67108864, 268435456, 1073741824, 4294967296, 17179869184, 68719476736, $2.74878*10$, or $1.09951*10^{12}$ members. In some cases, the library is a barcode library. In some cases, a barcode library may comprise at least about 1000, 10000, 100000, 1000000, 2500000, 5000000, 10000000, 25000000, 50000000, or 100000000 different barcode sequences.

The random barcode libraries may also comprise other polynucleotide sequences. In some cases, these other polynucleotide sequences are non-random in nature and include, for example, primer binding sites, annealing sites for the generation of forked adapters, immobilization sequences, and regions that enable annealing with a target polynucleotide sequence, and thus barcoding of the polynucleotide sequence.

In many cases, such libraries may be provided tethered to beads or particles for use in efficient delivery of the library elements. For example, in some cases, beads are provided having the tagging oligonucleotide structures described above, attached to them. In such cases, an individual bead may include oligonucleotides that include a first region that includes a transformable oligonucleotide sequence, e.g., as a transformable sequence, or sequence of transformable nucleotides. As noted above, this first region may be common to all of the oligonucleotides attached to a given bead, or among populations of beads. Alternatively, the first region may vary among different beads or different populations of beads. The oligonucleotides may also include additional regions or sequence segments, e.g., second, third, fourth, etc. regions, where such additional regions may include variable regions, e.g., that vary in sequence as between oligonucleotides on different beads. Such variable regions may include barcode sequences that differ among oligonucleotides on different beads. By providing a bead with a given barcode sequence segment, but where such barcode sequence differs on other beads, one can readily partition different barcodes into different partitions by merely partitioning the beads on an individual basis. Examples of partitioning methods for such barcode sequences are described in, e.g., Published U.S. Patent Application Publication Nos. 2014/0378345, and 2015/0292988, the full disclosures of each of which are incorporated herein by reference in their entirety for all purposes.

Partitioning methods can include flowing an aqueous fluid comprising a suspension of barcode sequences into a droplet generation junction comprising a partitioning fluid. During a window of droplet generation, the barcode sequences can be flowing into the droplet generation junction at a frequency that varies less than 30%. The method can also include partitioning the barcode sequences in the partitioning fluid during the window of droplet generation. Another partitioning method can include providing a gel precursor in an aqueous fluid and flowing the aqueous fluid having the gel precursor through a fluid conduit that is fluidly connected to a droplet generation junction comprising a partitioning fluid. The partitioning fluid can comprise a gel activation agent. The method can also include forming droplets of the aqueous fluid in the partitioning fluid, where, within the droplets, the gel activation agent contacts the gel precursor to form gel microcapsules.

Other variable regions may be provided within the oligonucleotide sequences, e.g., for use as random n-mer priming sequences, where such variability may exist as between oligonucleotide sequences on a given bead, as between individual beads, or as between bead populations. Likewise, the oligonucleotide sequences may include other common regions, such as common primer sequences, e.g., sequencer specific primer sequences, attachment sequences, and the like, that are common as to oligonucleotides on a given bead, as between two or more beads or as among a population of beads.

The tagging oligonucleotides may be attached to the beads through, e.g., a reversible or cleavable linkage, such that the oligonucleotides may be separated from the beads upon application of a stimulus, e.g., a chemical, thermal, optical, or mechanical stimulus. Examples of such cleavable linkages include, e.g., those described in Published U.S. Patent Application Publication Nos. 2014/0228255 and 2014/0378345, each of which is entirely incorporated herein by reference. In some cases, the beads themselves may comprise degradable structures, such as degradable polymers or hydrogels that may degrade to further facilitate the release of the oligonucleotides from the beads into a substantially homogenous reaction mixture. See, e.g., U.S. Patent Application Publication Nos. 2014/0228255 and 2014/0378345 each of which is entirely incorporated herein by reference.

Processes

Although described in some detail above for use in quantifying nucleic acid molecules, e.g., mRNA for expression analysis, the following example provides one detailed example of one type of specific process for employing transformable tagging moieties in such expression analysis.

In an exemplary process for evaluating expression of one or more genes in cell cultures, one may individually analyze the contents of the cells using processes, e.g., as described in U.S. Patent Application Publication No. 2015/0376609, which is incorporated herein by reference in its entirety for all purposes, and using the transformable tagging moieties described herein.

Methods of analyzing nucleic acids from cells include providing nucleic acids derived from an individual cell into a discrete partition; generating one or more first nucleic acid sequences derived from the nucleic acids within the discrete partition, which one or more first nucleic acid sequences have attached thereto oligonucleotides that comprise a common nucleic acid barcode sequence; generating a characterization of the one or more first nucleic acid sequences or one or more second nucleic acid sequences derived from the one or more first nucleic acid sequences, which one or more second nucleic acid sequences comprise the common barcode sequence; and identifying the one or more first nucleic acid sequences or one or more second nucleic acid sequences as being derived from the individual cell based, at least in part, upon a presence of the common nucleic acid barcode sequence in the generated characterization.

For example, these processes may be used in the analysis and quantification of gene expression within individual cells, either generally, or in response to certain stimuli.

In at least one approach, a set of tagging oligonucleotides may be employed that include a common, but transformable tagging segment in their sequence. Following tagging of individual expressed copies of one or more genetic elements, e.g., genes or gene fragments, referred to herein as expression products, these common tagging elements may be transformed such that for each individual expressed molecule, a unique, or substantially unique tagging element is created in a tagged copy of the expressed molecule, to allow the unique identification of that originating expressed copy. By counting the uniquely identifiable expressed copies, one can infer the number/quantity of the expressed copies of a given gene.

A simplified process is schematically illustrated in the flow chart provided in FIG. 2. In particular, at stage 202, a cell may express one or more genes in the form of messenger RNA (mRNA). At stage 204, the various individual mRNA molecules expressed by a given cell are subjected to tagging with an oligonucleotide sequence that includes a transformable tagging segment. The individual tagged mRNA molecules are then processed at stage 206 to transform the transformable tagging segment into a new tagging segment that is unique for each starting tagged mRNA molecule, e.g., as a tagged cDNA molecule. These resulting cDNA molecules may then be subjected to amplification processes at stage 208, while preserving the attribution of the resulting amplified material to its original starting molecule (based upon the transformed tagging segment). The amplified cDNA molecules and their associated tags may then be sequenced at stage 210. From the sequence data, one can identify sequences of a given gene at stage 212, and by virtue of the number of different tags associated with the sequences of that gene, identify or at least infer the number of starting expressed molecules for that gene.

In a more detailed discussion of an example process, a cell suspension may be subjected to co-partitioning into aqueous droplets in an oil emulsion, e.g., as described in U.S. Patent Publication No. 2015-0376609, filed Jun. 26, 2015, which is entirely incorporated herein by reference, using, e.g., a microfluidic droplet or emulsion generation system. A microcapsule may also be co-partitioned into the discrete droplets, where the microcapsules carry the tagging oligonucleotides coupled to the microcapsule in a releasable fashion, e.g., allowing release of the tagging oligonucleotides upon application of a stimulus to the content of the droplets. As described above, the oligonucleotides will typically comprise the transformable tagging sequence segment along with other functional sequence segments, e.g., other barcode segments, priming segments, attachment segments and the like. In this particular example, the tagging oligonucleotides also comprise a barcode segment that will be common for all tagging oligonucleotides on a given microcapsule, but which may vary among different microcapsules. By co-partitioning a single cell with a single microcapsule, this barcode can function as an address moiety to tag and identify all of the nucleic acids that are derived from the individual cell.

Following co-partitioning, the cells within the droplets may be lysed, e.g., through inclusion of a lysis agent within the droplet, e.g., a detergent, chaotropic agent or other lysing agent, or they may be lysed through the application of other stimuli, e.g., mechanical, thermal, electrical, etc. Once lysed, the contents of the cells, including the messenger RNA from expressed genes will be released into the droplets. Tagging oligonucleotides present on the co-partitioned microcapsules are also released into the droplet and may be configured to specifically interact with the mRNA molecules, e.g., by using a poly-T sequence segment as a capture/priming segment against the poly-A tail of the mRNA, e.g., as segment 104 in FIG. 1.

Figure 3:
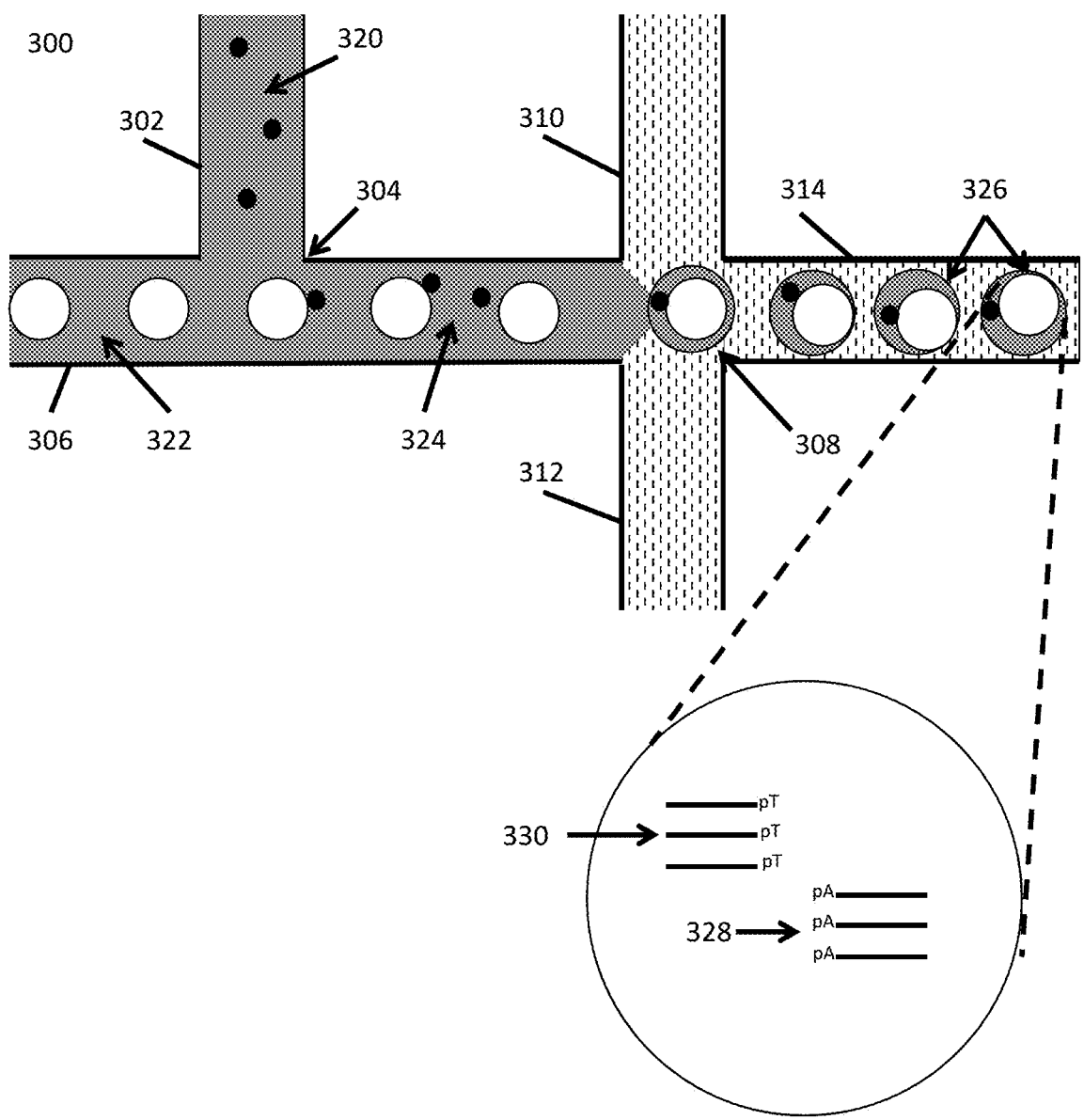
FIG. 3 provides a schematic illustration of a partitioning system and process for allocating tagging moieties to individual cells in a tagging process of the present disclosure.

The overall process is schematically illustrated in FIGS. 3 and 4. As shown in FIG. 3, individual cells of interest are co-partitioned along with individual microcapsules bearing tagging oligonucleotides as described herein, in a microfluidic channel network 300. The cell suspension 320 is passed through a first channel segment 302 to a first mixing junction, where it is co-mixed with a flowing suspension of microcapsules or beads 322 bearing the tagging oligonucleotides, coming into the junction 304 from another channel segment 306.

The microcapsule suspension may also include a lysis agent to be mixed with and act upon the cells once they are partitioned. The cells and microcapsules are flowed at a rate that allows enough space between adjacent microcapsules and adjacent cells, so as to increase the probability of co-partitioning of an individual cell with an individual microcapsule. The co-mixed suspension of cells and microcapsules 324 are them driven into a droplet generation 308 junction or partitioning junction, where they are focused by coaxial flows of oil streams coming in from side channels 310 and 312 such that individual droplets 326 of the aqueous co-mixed suspensions are formed in a flowing oil stream in outlet channel segment 314.

Once co-partitioned into a droplet, an individual cell, exposed to the lysis agent, will release its contents, e.g., mRNA molecules 328, into the droplet. Likewise, the microcapsule will release its payload of tagging oligonucleotides, e.g., tagging oligonucleotides 330, into the droplet as well. Once present in a homogeneous mixture within a given droplet, the tagging oligonucleotides may be used to tag fragments of the nucleic acids from the cells, and as described particularly here and as schematically illustrated in FIG. 4, mRNA molecules.

As shown in FIG. 4, tagging oligonucleotides 402 released from the microcapsule, by virtue of their inclusion of a poly-T sequence 404, will anneal with the poly-A tail 406 of the mRNA 408 released from an individual cell within the droplet. As described previously, the tagging oligonucleotides include both a common sequence of transformable nucleotides as the transformable tagging segment 410, along with a barcode segment 412 of oligonucleotides that is common to all of the oligonucleotides released from a given microcapsule. These barcodes serve to attribute resulting produced fragments as having originated from the same cell when all of the nucleic acids are later sequenced.

Following annealing of the tagging oligos 402 to the mRNA molecules 408, a reverse transcriptase enzyme, present within the aqueous droplet (and introduced with one of the cell suspension and/or the microcapsule suspension), is used to extend the tagging oligonucleotide 402 along the annealed mRNA 408, as shown by the dashed arrow, replicating the expressed gene portion 414 of the mRNA as a cDNA fragment 416 with the tagging oligonucleotide 402 attached. In many cases, the reverse transcriptase enzyme used will include terminal transferase activity, which will add a series of cytosine residues 418 to the 3' terminus of the tagged cDNA molecule 416. A template switch oligonucleotide 420, having a set of 3' guanosine residues is then annealed to the terminus of the cDNA molecule, and extended by the reverse transcriptase, in order to append an additional priming sequence 422 to the end of the resultant tagged cDNA molecule 424. At this point, the tagging oligonucleotide may include the same transformable tagging sequence 410 as other tagged mRNA replicate molecules within a given partition, or even within many or even all of the partitions.

As will be appreciated, with each successive replication of a transformable tagging segment, a new and differently tagged replicate will be produced. As such, in many cases, it will be desirable to control the number of replication cycles of the transformable sequence tagged mRNAs, e.g., to a single or few cycles of replication, e.g., 1-4 cycles, with single cycle replication preferred. Typically, thermal cycling operations may be used to control the number of cycle operations, e.g., exposing a given tagging operation to only a single melting, annealing and extension operation, to ensure that only one transformed tagged mRNA replicate is produced from each starting mRNA molecule.

As noted, the tagged cDNA molecule 424 is then subjected to a single replication round by priming a DNA polymerization extension from the appended primer region 422, using a DNA polymerase that is unbiased in its incorporation against the transformable nucleotides in the tagging segment 410 (while maintaining processivity across such nucleotides). Following a single round of replication, the resulting tagged replicate molecule 428 will include a new, transformed tagging segment 426, that will be substantially unique as compared to other replicated tagging segments present in the same reaction mixture, thus providing a level of uniqueness to the original molecule, despite being processed in the same manner as all other molecules in that reaction mixture.

As will be appreciated, the level of uniqueness of a given replicated tagging segment will depend upon the level of degeneracy, the number of transformable bases, and the number of molecules within a given process. In some cases, these parameters may be at a level where the molecules within a given analysis are tagged with complete uniqueness, e.g., no repeated transformed tagging elements within a given reaction mixture, while in other cases, the level of uniqueness will be at a level at which it may be expected that duplicate copies of a given gene, e.g., expression products, may be expected to be tagged with a unique tagging element relative to each other, but that absolute uniqueness may not exist. In other cases, the level of uniqueness will be that a given tagging segment may yield, following a single round of replication, at least 10 distinct transformed tagging segments (e.g., having at least 10 distinct nucleotide sequences), at least 50 distinct transformed tagging segments, at least 100 distinct transformed tagging segments, at least 200 distinct transformed tagging segments, at least 300 distinct transformed tagging segments, at least 400 distinct transformed tagging segments, at least 500 distinct transformed tagging segments, at least 1000 distinct transformed tagging segments, or in some cases, at least 1000 distinct transformed tagging segments from a common starting transformable tagging segment.

Following the single round of replication, the sample may be treated to remove the original tagging oligonucleotides, including the original tagged cDNA molecule, that contain the transformable tagging segments, in order to prevent the remaining transformable tagging oligonucleotides from participating in subsequent amplification operations and injecting new, transformed molecules into the analysis. Removal of these oligonucleotides may be carried out by a number of methods. For example, in some cases, the original tagging oligonucleotides may include a "handle" moiety that facilitates its removal from a reaction mixture, e.g., through affinity purification. Such handles may include, e.g., specific nucleic acid sequences that may hybridize to solid support-bound complementary probe sequences, to remove those from the reaction mixture. Alternatively, the handles may include other affinity binding reagents, e.g., biotin, avidin, streptavidin, or the like, that may be used to pull out the original transformable tagging oligonucleotides from the reaction mixture. Any of a wide variety of affinity reagents may be employed in this regard, e.g., nucleic acids, proteins, peptide, antigens, antibodies, or reactive portions of any of the foregoing.

In many cases, digestive removal processes may be used, in order to avoid material losses that may accompany the above-described purification processes. In particular, processes in which the transformable tagging oligonucleotides are preferentially digested or degraded may be used to remove them from participation in subsequent reaction operations. In an example, the original transformable tagging oligonucleotides may include specific regions or bases that allow for their selective digestion or removal. By way of example, the tagging oligonucleotides may include uracil-containing bases at one or more positions within the overall oligonucleotide sequence. Treatment of the reaction mixture with a uracil targeting digestion process, e.g., uracil DNA glycosylase enzyme followed by DNA glycosylase endonuclease VIII treatment, e.g., USER, then allows targeted digestion of the original tagging oligonucleotide sequences, while the replicates containing the transformed tagging segments will contain no uracil containing bases. Alternatively, the tagging oligonucleotides may include specific restriction endonuclease cleavage sites, which, when contacted with the relevant endonuclease enzyme, results in cleavage of the transformable tagging oligonucleotides. Additionally or alternatively, replication processes following the tagging process may be carried out using primer sequences that include 5' protected groups, such as phosphorothioate groups, such that those replicate molecules produced in a first replication round are protected from 5' to 3' exonuclease digestion of double stranded DNA substrate, e.g., using a T7 exonuclease, while the originating molecules may be subject to digestion. Similarly, tagging oligonucleotides may be provided with other properties rendering them susceptible to digestion, e.g., incorporating RNA bases, such that the tagging oligonucleotides may be digested using nucleases specific for RNA substrates, e.g., ribonucleases.

In another approach, the tagging oligonucleotides may incorporate sequence components that prevent them from participating in subsequent replication events after a first round of replication. By way of example, the original tagging oligonucleotides may include sequence elements, such as uracil containing bases that can prevent their replication by certain polymerases, e.g., that are present in later rounds of replication. In a first round of replication following the creation of the tagged cDNA molecule 424, a heat labile polymerase, e.g., DNA PolI, Klenow, which may be unbiased for the transformable bases in the tagging segment 410, but is capable of processing through uracil containing bases, is used to carry out a first round of replication resulting in creation of the transformed tagged oligonucleotide 428 that includes no uracil bases. Following the first round of replication, elevation of the reaction temperature to an appropriate melting temperature, e.g., 90 C, will melt the replicate strand 428 from the original tagged cDNA 424, while also inactivating the first polymerase enzyme. A second, heat stable polymerase, also present in the reaction mix, and which is not capable of replicating through uracil containing bases, e.g., archeal polymerases such as 9 degrees north, deep vent, and the like, will then remain active in subsequent amplification operations, to selectively amplify the replicate transformed tagged oligonucleotide 428, while not replicating any of the original tagging oligonucleotides, e.g., tagged cDNA 424, or any remaining but unincorporated tagging oligonucleotides 402. In alternative arrangements, these polymerases may be present iteratively. For example, a first uracil processing polymerase is present in the first round of replication. Following this first round of replication, this first polymerase may be removed, e.g., by purifying the nucleic acids away from the polymerase, and the second, polymerase, which is incapable of replicating against uracil containing bases may be introduced. The presence of the uracils in the original tagging moiety may then prevent further replication of the original tagging segment, and consequent generation of new transformed tagging oligonucleotides. Instead, only direct complements/replicates of the transformed oligonucleotides may be created in these subsequent replication rounds.

While the above is described in terms of a single round of replication of the tagged cDNA molecule 424, it will be appreciated that additional rounds of replication, e.g., 2, 3, 4, 5, or more, may be practiced within the context of the processes described herein, by allowing for deconvolution of additional tags imparted to a given analysis. For example, knowing the number of expected additional unique tagging molecules added by virtue of additional rounds of transforming replication, one may account for the additional level of diversity in the resulting molecules, in order to extrapolate the original number of starting molecules.

In some cases, the needed diversity, and thus, the makeup of a transformable sequence segment may be calculated. In particular, to calculate the effective diversity of a sequence, one may determine it as a function of the level of degeneracy of the transformable bases and the number of such transformable bases in each tagging sequence segment. Using the so-called birthday problem one may calculate the expected number of molecules that will share the same tag. The effective diversity can be calculated by first measuring the output of the process with a detector (e.g., sequencing a population of sequence segments including the degenerate bases) and counting the frequency of observed bases at each transformable site. One may then use a diversity index to compute the effective diversity at each site. An example of such a value may be the exponent of the Shannon entropy of each transformable base, times the number of such bases in the tag. The ideal, unbiased 4-way degenerate base has a diversity of 4. A normal, canonical base, in contrast, may have a diversity of 1 (i.e., it will always be observed as being itself). Once armed with this (experimentally determined) value for a base, and the number of bases, one can map this to the space of integers from 1 to N where N is simply the (effective diversity)×(number of transformable bases). Applying the following formula for counting the expected number of collisions when sampling from this integer space gives the expected number of duplicated sequences (note that this is analogous to the problem of computing the number of collisions produced by a hash function in computer science), where the probability that the kth integer randomly chosen from [1,d] will repeat at least one previous choice equals q(k−1; d) above. The expected total number of times a selection will repeat a previous selection as n such integers are chosen, equals:

$$\sum_{k=1}^{n} q(k-1;d) = n - d + d\left(\frac{d-1}{d}\right)^n$$

Following creation of the more uniquely tagged replicates of the original sequence segments, the transformed tagged oligonucleotides may be subjected to additional processing operations in order to facilitate their analysis. For example, in some cases, the transformed tagged molecules may be subjected to amplification, e.g., using PCR, in order to produce sufficient quantities of molecules for analysis, e.g., using nucleic acid arrays or nucleic acid sequencing systems.

In the case of PCR amplification, the transformed tagged molecules may be processed to add amplification priming sequences to one or both ends of the tagged molecules. In some cases, the tagging moiety may include priming sequences that may be exploited as amplification primers, as described above. Additional priming sequences may be added to the opposing ends of the tagged segment through, e.g., ligation, or polymerase extension of amplification primers coupled to random priming sequences, providing replicate sequences for amplification.

The use of various approaches for producing amplifiable tagged nucleic acid molecules is described, for example, in published U.S. Patent Application Publication Nos. 2014/0378345, 2014/0228255, the full disclosures of which are hereby incorporated herein by reference in their entirety for all purposes.

Nucleic amplification is a method for creating multiple copies of small or long segments of DNA. DNA amplification may be used to attach one or more desired oligonucleotide sequences to individual beads, such as a barcode sequence or random N-mer sequence. DNA amplification may also be used to prime and extend along a sample of interest, such as genomic DNA, utilizing a random N-mer sequence, in order to produce a fragment of the sample sequence and couple the barcode associated with the primer to that fragment.

For example, a nucleic acid sequence may be amplified by co-partitioning a template nucleic acid sequence and a bead comprising a plurality of attached oligonucleotides (e.g., releasably attached oligonucleotides) into a partition (e.g., a droplet of an emulsion, a microcapsule, or any other suitable type of partition, including a suitable type of partition described elsewhere herein). The attached oligonucleotides can comprise a primer sequence (e.g., a variable primer sequence such as, for example, a random N-mer, or a targeted primer sequence such as, for example, a targeted N-mer) that is complementary to one or more regions of the template nucleic acid sequence and, in addition, may also comprise a common sequence (e.g., such as a barcode sequence). The primer sequence can be annealed to the template nucleic acid sequence and extended (e.g., in a primer extension reaction or any other suitable nucleic acid amplification reaction) to produce one or more first copies of at least a portion of the template nucleic acid, such that the one or more first copies comprises the primer sequence and the common sequence. In cases where the oligonucleotides comprising the primer sequence are releasably attached to the bead, the oligonucleotides may be released from the bead prior to annealing the primer sequence to the template nucleic acid sequence. Moreover, in general, the primer sequence may be extended via a polymerase enzyme (e.g., a strand displacing polymerase enzyme as described elsewhere herein, an exonuclease deficient polymerase enzyme as described elsewhere herein, or any other type of suitable polymerase, including a type of polymerase described elsewhere herein) that is also provided in the partition. Furthermore, the oligonucleotides releasably attached to the bead may be exonuclease resistant and, thus, may comprise one or more phosphorothioate linkages as described elsewhere herein. In some cases, the one or more phosphorothioate linkages may comprise a phosphorothioate linkage at a terminal internucleotide linkage in the oligonucleotides.

In some cases, after the generation of the one or more first copies, the primer sequence can be annealed to one or more of the first copies and the primer sequence again extended to produce one or more second copies. The one or more second copies can comprise the primer sequence, the common sequence, and may also comprise a sequence complementary to at least a portion of an individual copy of the one or more first copies, and/or a sequence complementary to the variable primer sequence. The aforementioned operations may be repeated for a desired number of cycles to produce amplified nucleic acids.

The oligonucleotides described may comprise a sequence segment that is not copied during an extension reaction (such as an extension reaction that produces the one or more first or second copies described above). As described elsewhere herein, such a sequence segment may comprise one or more uracil containing nucleotides and may also result in the generation of amplicons that form a hairpin (or partial hairpin) molecule under annealing conditions.

A plurality of different nucleic acids can be amplified by partitioning the different nucleic acids into separate first partitions (e.g., droplets in an emulsion) that each comprise a second partition (e.g., beads, including a type of bead described elsewhere herein). The second partition may be releasably associated with a plurality of oligonucleotides. The second partition may comprise any suitable number of oligonucleotides (e.g., more than 1,000 oligonucleotides, more than 10,000 oligonucleotides, more than 100,000 oligonucleotides, more than 1,000,000 oligonucleotides, more than 10,000,000 oligonucleotides, or any other number of oligonucleotides per partition described herein). Moreover, the second partitions may comprise any suitable number of different barcode sequences (e.g., at least 1,000 different barcode sequences, at least 10,000 different barcode sequences, at least 100,000 different barcode sequences, at least 1,000,000 different barcode sequences, at least 10,000,000 different barcode sequence, or any other number of different barcode sequences described elsewhere herein).

Furthermore, the plurality of oligonucleotides associated with a given second partition may comprise a primer sequence (e.g., a variable primer sequence, a targeted primer sequence) and a common sequence (e.g., a barcode sequence). Moreover, the plurality of oligonucleotides associated with different second partitions may comprise different barcode sequences. Oligonucleotides associated with the plurality of second partitions may be released into the first partitions. Following release, the primer sequences within the first partitions can be annealed to the nucleic acids within the first partitions and the primer sequences can then be extended to produce one or more copies of at least a portion of the nucleic acids with the first partitions. In general, the one or more copies may comprise the barcode sequences released into the first partitions.

Nucleic acid (e.g., DNA) amplification may be performed on contents within fluidic droplets. Fluidic droplets may contain oligonucleotides attached to beads. Fluidic droplets may further comprise a sample. Fluidic droplets may also comprise reagents suitable for amplification reactions which may include Kapa HiFi Uracil Plus, modified nucleotides, native nucleotides, uracil containing nucleotides, dTTPs, dUTPs, dCTPs, dGTPs, dATPs, DNA polymerase, Taq polymerase, mutant proof reading polymerase, 9 degrees North, modified (NEB), exo (−), exo (−) Pfu, Deep Vent exo (−), Vent exo (−), and acyclonucleotides (acyNTPS).

Oligonucleotides attached to beads within a fluidic droplet may be used to amplify a sample nucleic acid such that the oligonucleotides become attached to the sample nucleic acid. The sample nucleic acids may comprise virtually any nucleic acid sought to be analyzed, including, for example, whole genomes, exomes, amplicons, targeted genome segments e.g., genes or gene families, cellular nucleic acids, circulating nucleic acids, and the like, and, as noted above, may include DNA (including gDNA, cDNA, mtDNA, etc.) RNA (e.g., mRNA, rRNA, total RNA, etc.). Preparation of such nucleic acids for barcoding may generally be accomplished by methods that are readily available, e.g., enrichment or pull-down methods, isolation methods, amplification methods etc. In order to amplify a desired sample, such as gDNA, the random N-mer sequence of an oligonucleotide within the fluidic droplet may be used to prime the desired target sequence and be extended as a complement of the target sequence. In some cases, the oligonucleotide may be released from the bead in the droplet, as described elsewhere herein, prior to priming. For these priming and extension processes, any suitable method of DNA amplification may be utilized, including polymerase chain reaction (PCR), digital PCR, reverse-transcription PCR, multiplex PCR, nested PCR, overlap-extension PCR, quantitative PCR, multiple displacement amplification (MDA), or ligase chain reaction (LCR). In some cases, amplification within fluidic droplets may be performed until a certain amount of sample nucleic acid comprising barcode may be produced. In some cases, amplification may be performed for about 1, 2, 3, 4, 5, 6, 7, 8, 9, 10, 11, 12, 13, 14, 15, 16, 17, 18, 19, or 20 cycles. In some cases, amplification may be performed for more than about 1, 2, 3, 4, 5, 6, 7, 8, 9, 10, 11, 12, 13, 14, 15, 16, 17, 18, 19, 20 cycles, or more. In some cases, amplification may be performed for less than about 2, 3, 4, 5, 6, 7, 8, 9, 10, 11, 12, 13, 14, 15, 16, 17, 18, 19, or 20 cycles.

Following initial processing operations, the resulting library of tagged nucleic acid molecules may be subjected to sequencing to determine the overall sequence of the library molecules. By identifying the number of different transformed tagging segments, one may infer a quantitation of the number of original starting molecules, including determining a predicted or expected number of starting molecules. Quantitation of (or quantifying) starting molecules, as used herein, refers to a general quantitation, rather than a specific and definitive quantitation. Such general quantitation may be generally used as a relative metric, e.g., to compare quantity metrics from two or more samples, the same or different samples but multiple time-points, samples in response to stimuli, etc., or may be used as a general indication of approximate numbers of starting molecules without requiring a definitive and absolutely accurate determination of the precise number of molecules.

Kits

Also provide herein are reagent kits and systems useful in practicing the methods and processes set forth above. As will be appreciated, the kits may generally include various reagents useful in carrying out these methods. For example, kits for use in practicing the described processes may generally include the tagging compositions described above, such as, for example, oligonucleotides comprising the transformable tagging segments described above. In some cases, the kits may include diverse libraries of such compositions that include large numbers of diverse oligonucleotides that comprise diverse barcode segments in conjunction with transformable tagging segments that may be common among some or all of the library members, but that will yield diversity of such tagging segments when transformed. In some case, these oligonucleotide libraries may be bund to particles, such as gel beads or microcapsules, and may, in some cases, include additional sequence elements within the oligonucleotides, e.g., sequencer specific priming and/or attachment sequences, e.g., as described in Published U.S. Patent Application Publication Nos. 2014/0378345, 2014/0228255, 2015/0376700, 2015/0376605, and 2016/0122817, the full disclosures of which are hereby incorporated herein by reference in their entirety for all purposes.

Oligonucleotides incorporating barcode sequence segments, which function as a unique identifier, may also include additional sequence segments. Such additional sequence segments may include functional sequences, such as primer sequences, primer annealing site sequences, immobilization sequences, or other recognition or binding sequences useful for subsequent processing, e.g., a sequencing primer or primer binding site for use in sequencing of samples to which the barcode containing oligonucleotide is attached. Further, as used herein, the reference to specific functional sequences as being included within the barcode containing sequences also envisioned the inclusion of the complements to any such sequences, such that upon complementary replication will yield the specific described sequence.

In addition, the kits may also include other reagents, such as enzymes, used for carrying out the processes described herein, including, for example, reverse transcriptases, DNA polymerases, e.g., Klenow, DNA Poll, Phi29 and/or archeal polymerases such as 9 degrees north, deep vent, and the like. Other enzymes may likewise be included, such as ligation enzymes, USER enzymes, CRISPR-Cas9 related enzymes, PCR amplification enzymes, e.g., Taq polymerases, etc., and the like.

In some cases, the kits described herein may also include reagents and components useful in partitioning sample materials, such as cells, nucleic acids, etc., into individual partitions such as droplets in an emulsion. These reagents and components may include, e.g., partitioning oils, such as fluorinated oils, fluorinated surfactants, and microfluidic devices, for use in generating emulsions of partitioned sample materials, reagents and tagging oligonucleotides as described herein. These components may be provided in conjunction with and/or for use on appropriate instrumentation systems designed to drive the fluids through the microfluidic devices in order to create the partitioned reagent emulsions as described. Examples of partitioning reagents, microfluidic devices and instrument systems are described in, e.g., Published U.S. Patent Application Publication Nos. 2010/0105112, 2015/0292988, 2014/0378345, 2014/0228255, and the full disclosures of which are hereby incorporated herein by reference in their entirety for all purposes.

The emulsions of the present invention may be formed using any suitable emulsification procedure known to those of ordinary skill in the art. In this regard, it will be appreciated that the emulsions can be formed using microfluidic systems, ultrasound, high pressure homogenization, shaking, stirring, spray processes, membrane techniques, or any other appropriate method. In one particular embodiment, a micro-capillary or a microfluidic device is used to form an emulsion. The size and stability of the droplets produced by this method may vary depending on, for example, capillary tip diameter, fluid velocity, viscosity ratio of the continuous and discontinuous phases, and interfacial tension of the two phases. Droplets of varying sizes and volumes may be generated within the microfluidic system. These sizes and volumes can vary depending on factors such as fluid viscosities, infusion rates, and nozzle size/configuration. Droplets may be chosen to have different volumes depending on the particular application. For example, droplets can have volumes of less than 1 .mu.l (microliter), less than 0.1 .mu.L (microliter), less than 10 mL, less than 1 mL, less than 0.1 mL, or less than 10 pL.

The kits may also include instructions for using the provided reagents and components in carrying out the processes described herein, as well as instructions and software for analysis of resulting data. The instructions may be printed in one or more documents or provided electronically, such as in an electronic file or in a user interface (UI), such as a graphical user interface (GUI), on an electronic device of a user.

Methods and systems of the present disclosure may be performed by a computer system that includes one or more computer processors and computer memory. Aspects of the systems and methods provided herein can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

Examples

A summary experiment was performed in which a first strand was synthesized across a sequence containing 1 of 7 transformable or degenerate bases, where the synthesis was carried out by 1 of 3 different polymerase enzymes. The first strand was synthesized using a primer containing 4 phosphorothioates on the 5' end of the extension primer so that T7 exonuclease may be used to degrade the template strand containing the transformable base while leaving the synthesized first stand intact. Sequencing results showed a wide range of incorporation patterns and polymerase efficiencies across the seven bases and three enzymes. By embedding the transformable base within a randomer we were able to identify combinations of flanking bases that maximize the effective diversity at the transformable base site by, e.g., affecting the kinetics of the polymerase as it approaches the transformable base or by affecting stacking interactions in the template-synthesized strand duplex at the transformable base site. In certain cases, while different configurations yielded different levels of diversity, one optimal combination appeared to include Taq polymerase with one or both of 5-nitroindole or deoxyisoguanosine.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A method of processing a plurality of nucleic acids, comprising:
   (a) co-partitioning (i) a plurality of oligonucleotide tagging moieties and (ii) a single cell comprising the plurality of nucleic acids in a partition;
   (b) in the partition, releasing the plurality of nucleic acids from the single cell;
   (c) attaching an oligonucleotide tagging moiety of the plurality of oligonucleotide tagging moieties to each of the plurality of nucleic acids to generate a plurality of tagged nucleic acids, wherein the oligonucleotide tagging moiety comprises one or more nucleotides each comprising a degenerate base, the one or more nucleotides having a variable complement when processed by a polymerase; and (d) processing the plurality of tagged nucleic acids with the polymerase to generate a tagged replicate molecule, wherein the tagged replicate molecule comprises random or semi-random complement bases incorporated into a position of the one or more degenerate bases.

2. The method of claim 1, wherein a nucleotide of the one or more nucleotides comprises 2-way degeneracy.

3. The method of claim 1, wherein a nucleotide of the one or more nucleotides comprises 3-way degeneracy.

4. The method of claim 1, wherein a nucleotide of the one or more nucleotides comprises 4-way degeneracy.

5. The method of claim 1, wherein the one or more nucleotides are selected from the group consisting of inosine, deoxyinosine, deoxyxanthine, 2'-deoxynebularine, 2'-deoxyguanosine, 5-nitroindole, 3-nitroindole, N6-methoxy-2,6-diaminopurine, 6H,8H-3,4-dihydropyrimido[4,5-c][1,2]oxazin-7-one, and a non-deoxy or a ribo version of each of the foregoing.

6. The method of claim 1, wherein the one or more nucleotides comprise from 1 to 20 nucleotides.

7. The method of claim 1, wherein the oligonucleotide tagging moiety further comprises one or more additional oligonucleotide segments.

8. The method of claim 7, wherein the one or more additional oligonucleotide segments are selected from the group consisting of primer sequence segments, hybridization sequence segments configured to hybridize to a target sequence, ligation sequence segments comprising one or more sequence overhangs and bridging or split sequences configured to facilitate ligation to a given sequence, sequencer surface attachment segments, and barcode sequence segments.

9. The method of claim 7, wherein the one or more additional oligonucleotide segments comprises a primer sequence wherein the primer sequence comprises a random primer sequence or a sequencing primer.

10. The method of claim 7, wherein the one or more additional oligonucleotide segments comprises a hybridization sequence.

11. The method of claim 10, wherein the hybridization sequence comprises a poly-T sequence.

12. The method of claim 1, wherein the plurality of oligonucleotide tagging moieties comprises a poly-T sequence segment, and the plurality of nucleic acids comprises mRNA molecules.

13. A method of processing nucleic acids, comprising:
(a) co-partitioning (i) a plurality of oligonucleotide tagging moieties and (ii) a single cell comprising a plurality of nucleic acids in a partition;
(b) in the partition, releasing the plurality of nucleic acids from the single cell;
(c) attaching an oligonucleotide tagging moiety of the plurality of oligonucleotide tagging moieties to each of the plurality of nucleic acids to generate a plurality of tagged nucleic acids, wherein the oligonucleotide tagging moiety comprises one or more degenerate bases having variable complements when processed by a polymerase;
(d) replicating the plurality of tagged nucleic acids with the polymerase to generate a tagged replicate molecule, wherein the tagged replicate molecule comprises random or semi-random complement bases incorporated into a position of the one or more degenerate bases; and
(e) sequencing the tagged replicate molecule.

* * * * *